United States Patent [19]

Pietroski et al.

[11] Patent Number: 5,722,401
[45] Date of Patent: Mar. 3, 1998

[54] ENDOCARDIAL MAPPING AND/OR ABLATION CATHETER PROBE

[75] Inventors: Susan M. Pietroski, Menlo Park; Andrew L. Lerohl, San Jose; Harold A. Heitzmann, Cupertino; Mir A. Imran, Los Altos Hills, all of Calif.

[73] Assignee: Cardiac Pathways Corporation, Sunnyvale, Calif.

[21] Appl. No.: 555,927

[22] Filed: Nov. 13, 1995

Related U.S. Application Data

[63] Continuation-in-part of Ser. No. 326,666, Oct. 19, 1994, abandoned.
[51] Int. Cl.$^6$ ................................. A61B 5/04; A61N 1/05
[52] U.S. Cl. .................................. 128/642; 607/122
[58] Field of Search ................... 128/642, DIG. 22; 607/119–122, 126, 127, 130; 606/41

[56] References Cited

U.S. PATENT DOCUMENTS

| 4,522,212 | 6/1985 | Gelinas et al. | |
|---|---|---|---|
| 4,699,147 | 10/1987 | Chilson et al. | |
| 5,156,151 | 10/1992 | Imran | 128/642 |
| 5,607,462 | 3/1997 | Imran | |

Primary Examiner—Jeffrey R. Jastrzab
Attorney, Agent, or Firm—Flehr Hohbach Test Albritton & Herbert LLP

[57] ABSTRACT

A catheter probe comprising a flexible elongate tubular member having proximal and distal extremities. An expandable assembly capable of moving from a contracted position to an expanded position is secured to the distal extremity of the flexible elongate tubular member and is formed from at least two elongate members movable between contracted and expanded positions. The elongate members have extremities which are joined so that the elongate members extend at an angle relative to each other to form a vee therebetween. A plurality of longitudinally and radially spaced-apart electrodes are carried by the expandable assembly so that they can be moved into engagement with the wall of the heart when the expandable assembly is expanded into the expanded position. Electrical conductors extend through the elongate tubular member and are connected to the electrodes for performing electrical functions with respect to the electrodes. An elastomeric material is adhered to the joined extremities of the elongate members and is disposed within the vee for inhibiting the formation of thrombus on the elongate members while the expandable assembly is disposed within the blood of the heart.

45 Claims, 10 Drawing Sheets

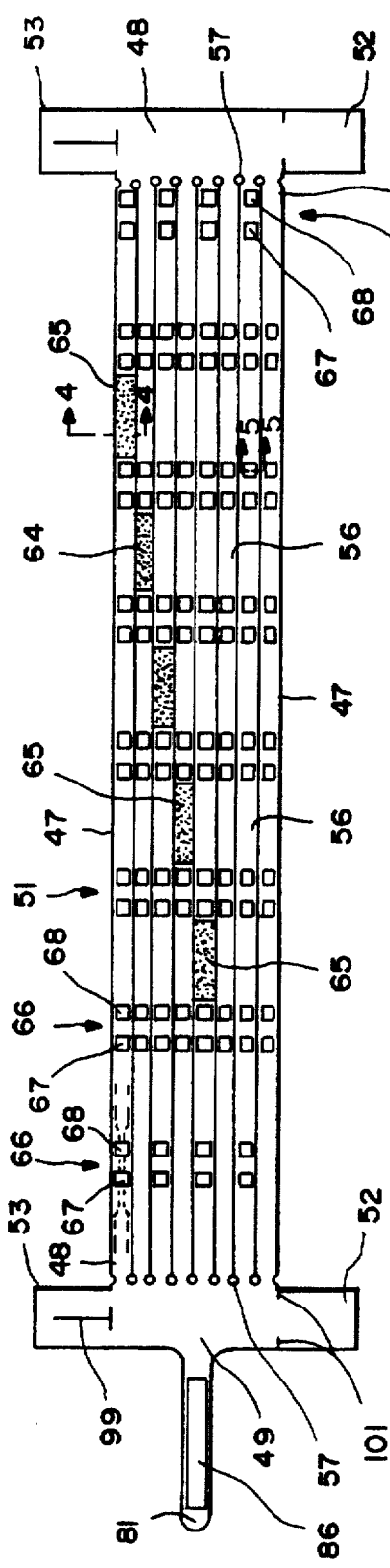
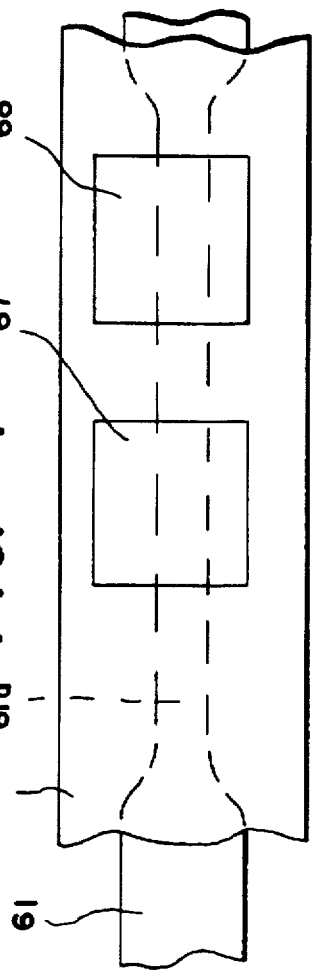
FIG.-2
FIG.-5
FIG.-4
FIG.-3

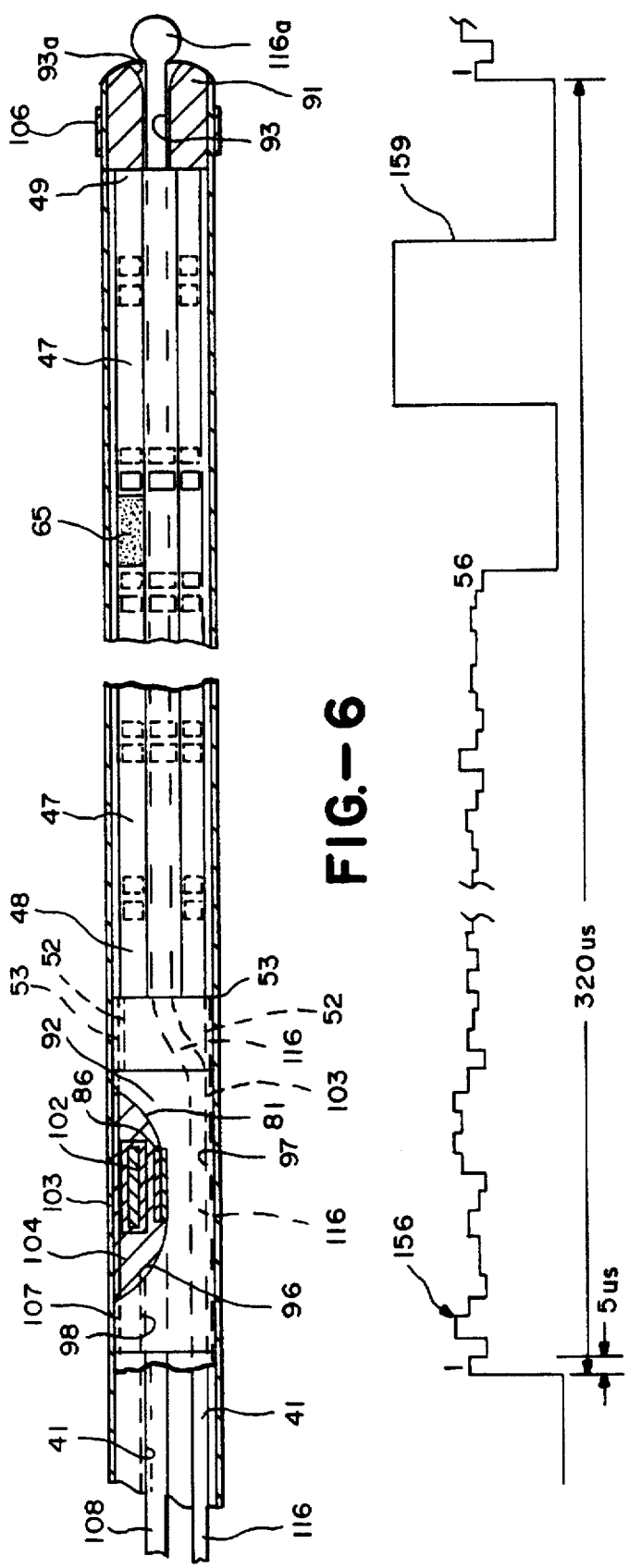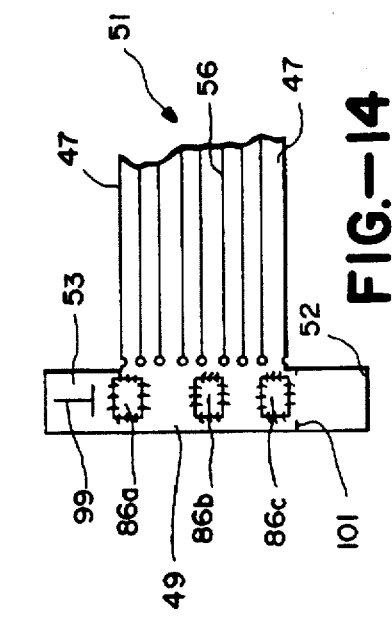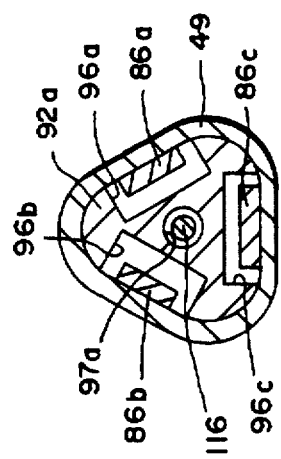

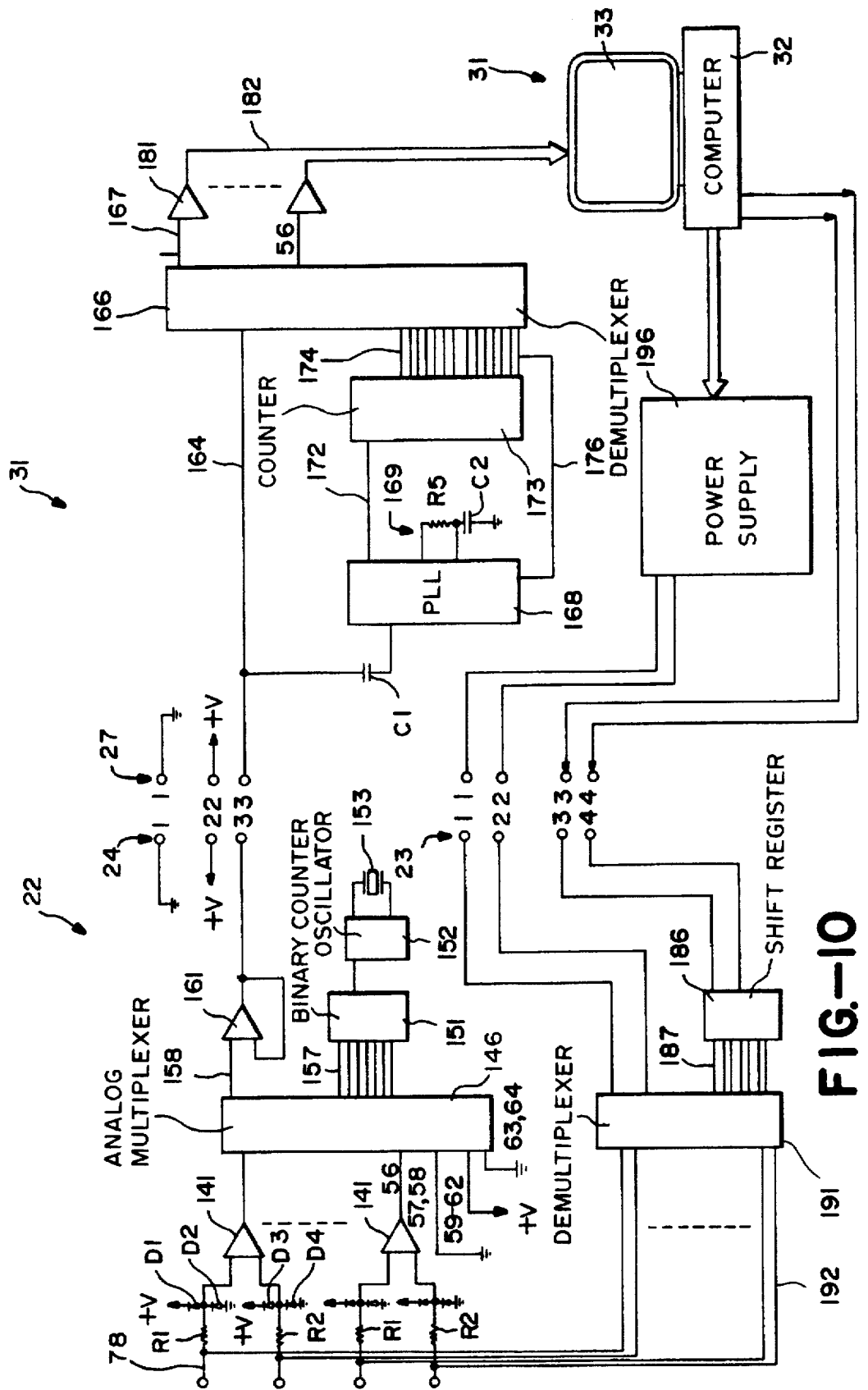

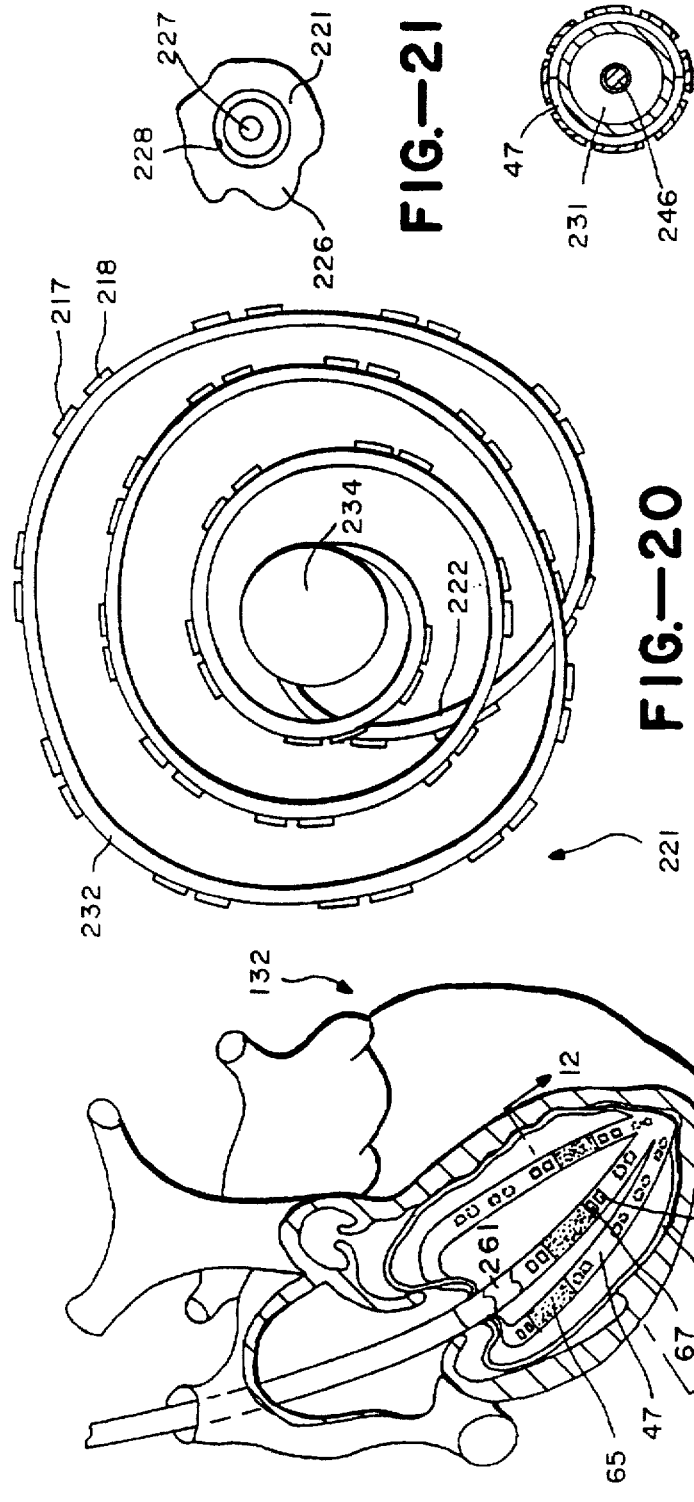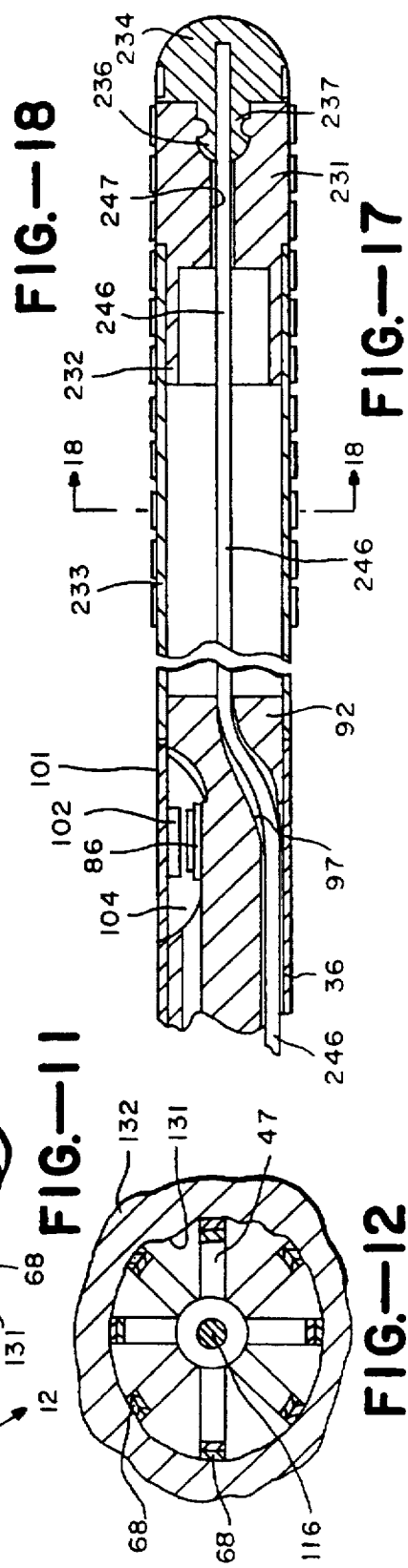

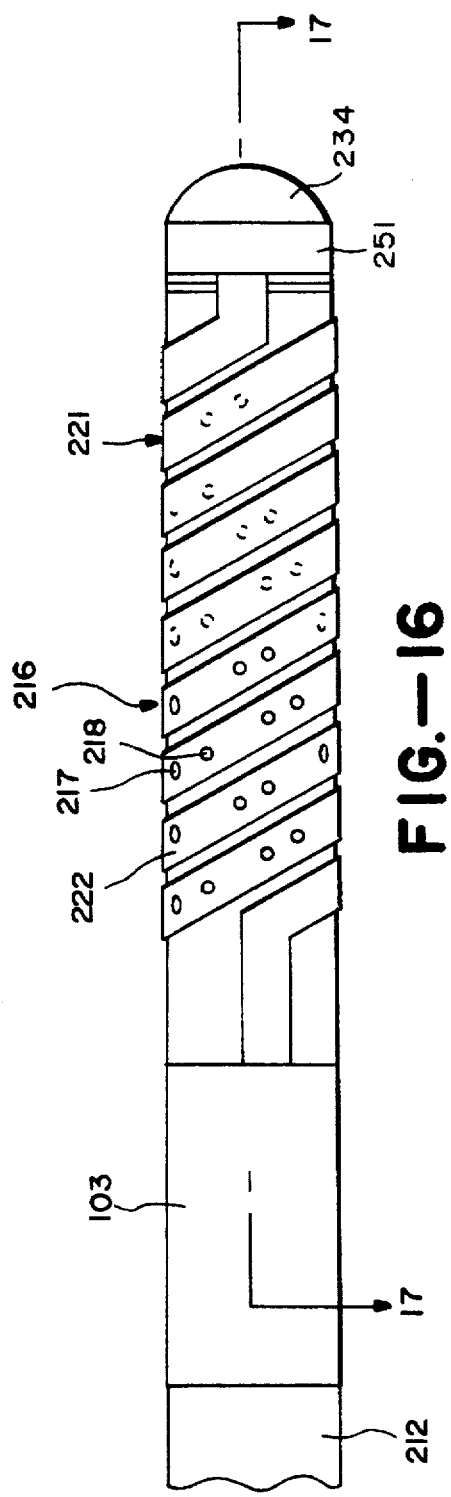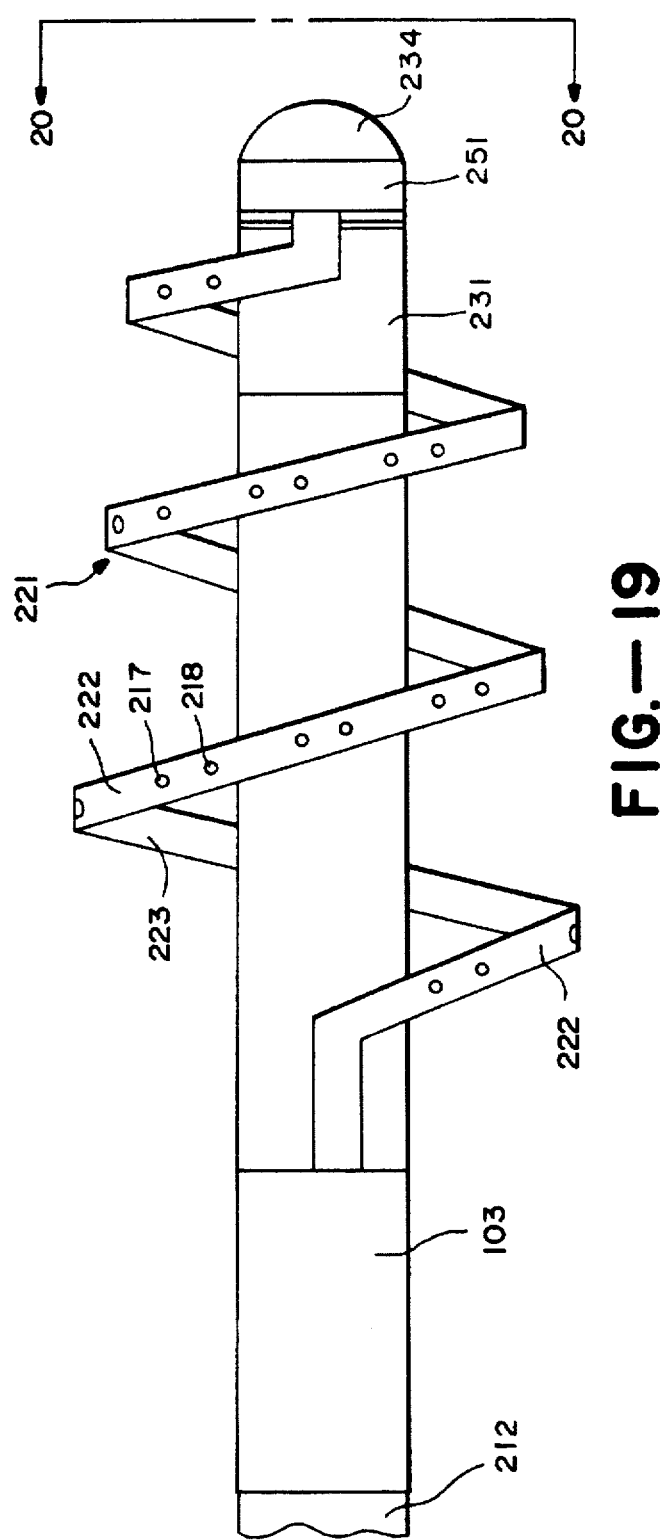

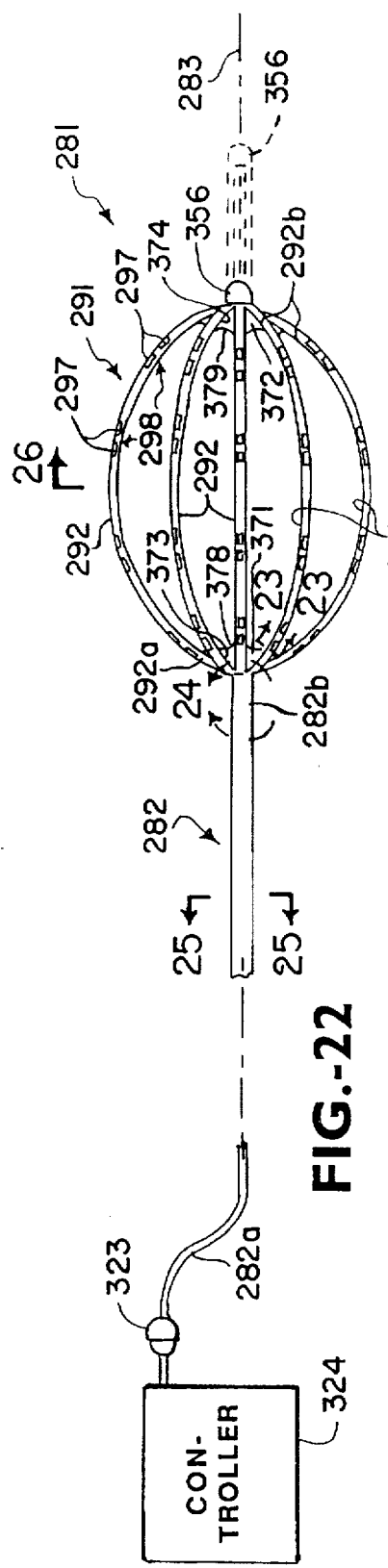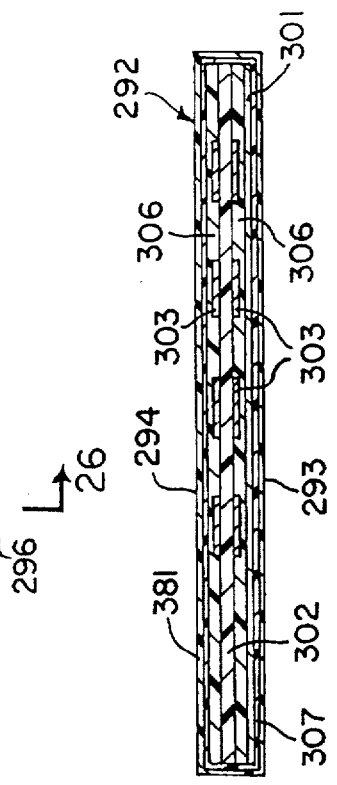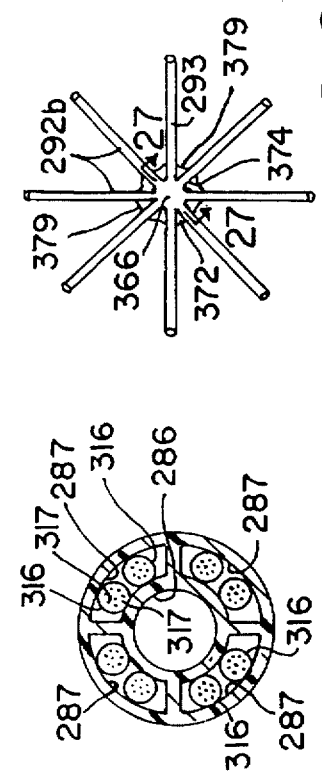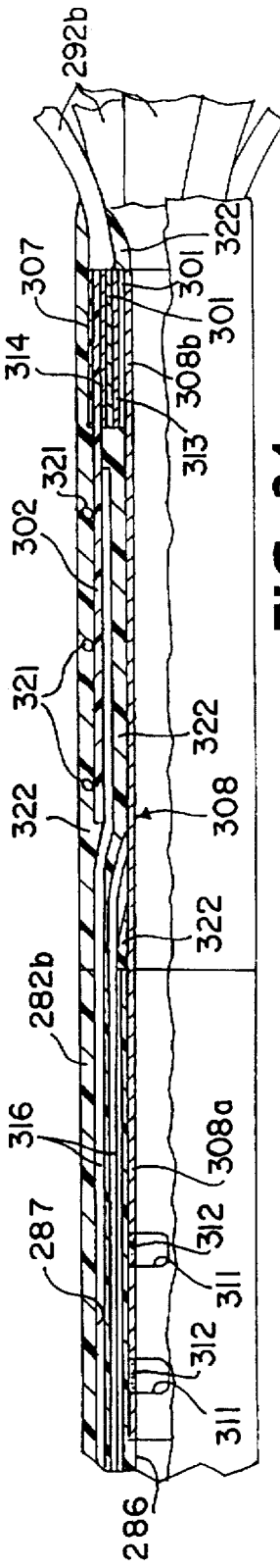

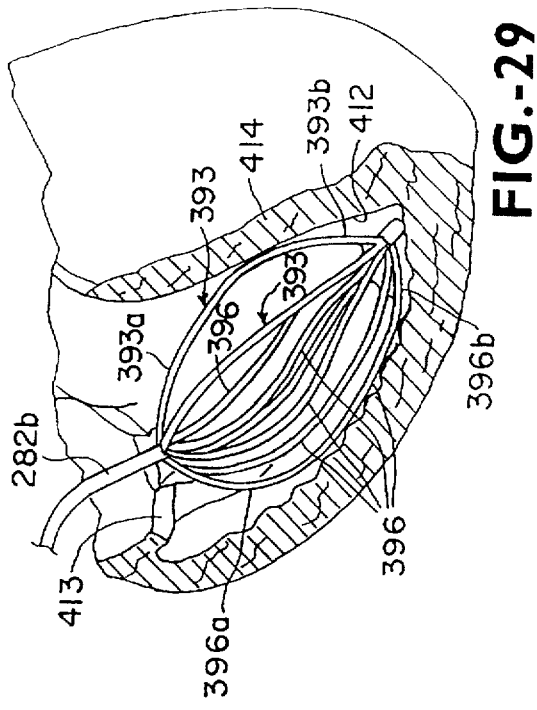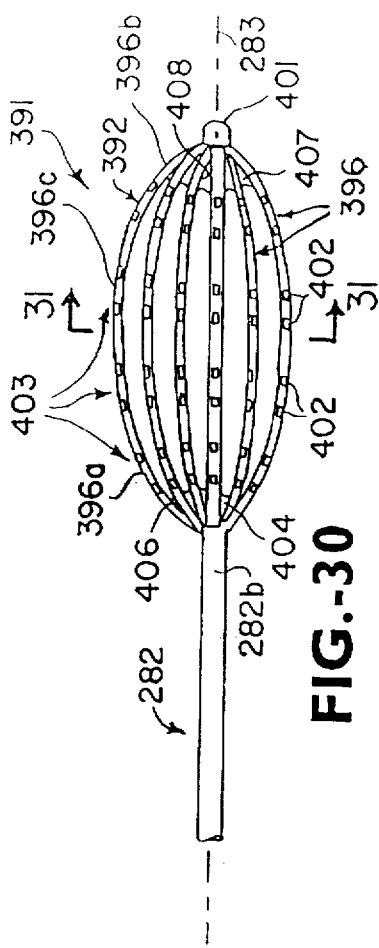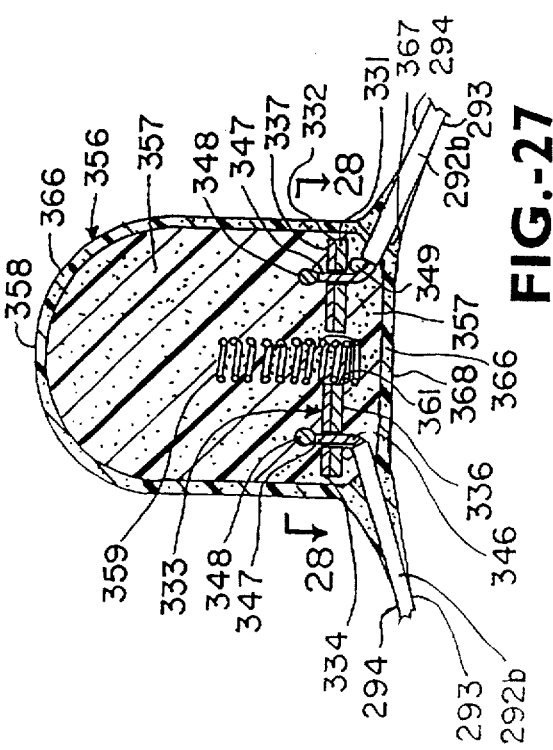

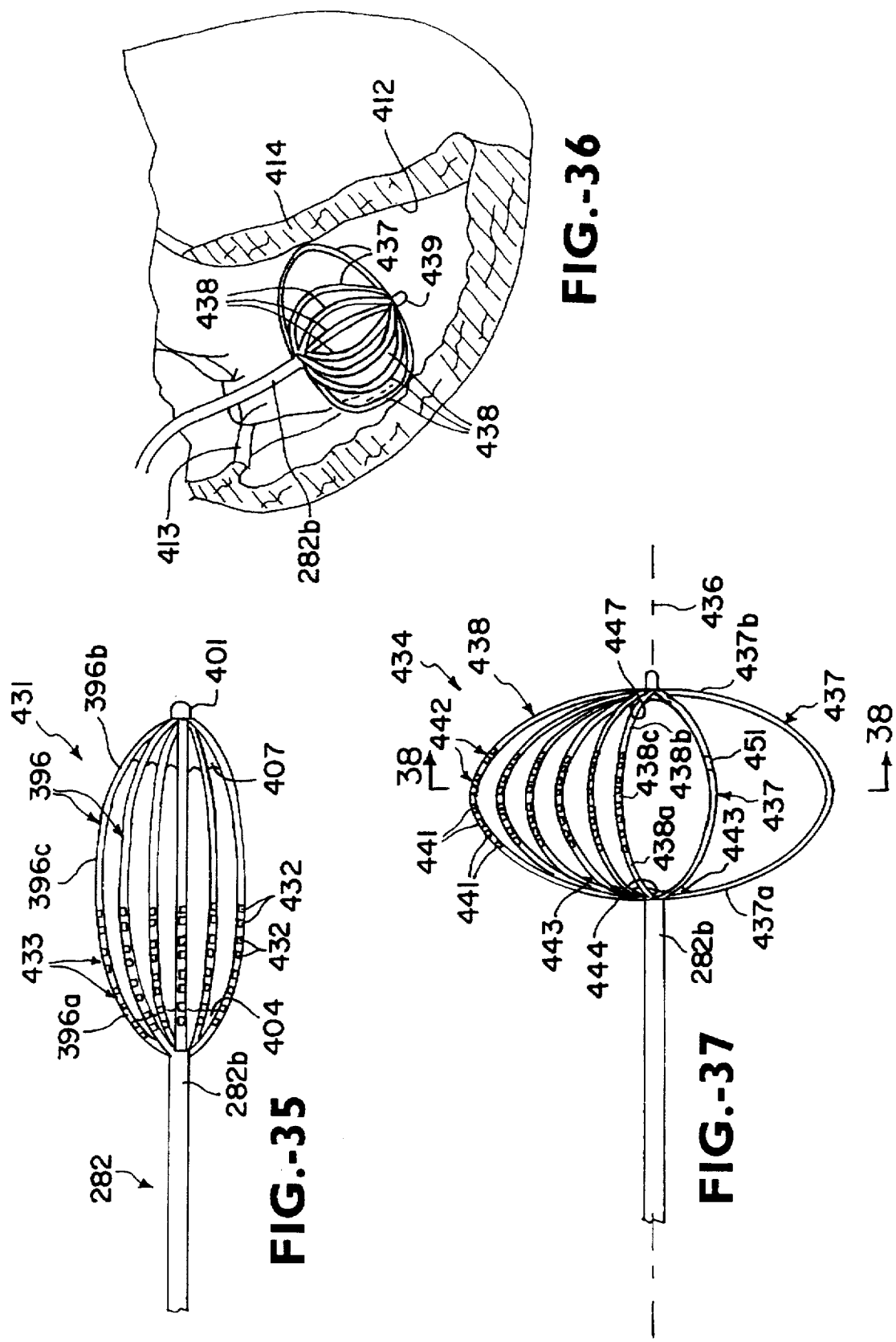

ENDOCARDIAL MAPPING AND/OR ABLATION CATHETER PROBE

CROSS-REFERENCE TO RELATED APPLICATIONS

This is a continuation-in-part of U.S. application Ser. No. 08/326,666 filed Oct. 19, 1994, now abandoned.

BACKGROUND OF THE INVENTION

1. Field of the Invention

This invention relates to an endocardial mapping and/or ablation catheter probe and method of treatment.

2. Description of the Related Art

Endocardial mapping and ablation catheters have heretofore been provided. However, they have been of limited capability particularly because they only have very few electrodes which makes it difficult to map accurately the electrical potentials in the walls forming the chambers of the heart, as for example the right ventricle. In order to obtain information from several different sites, it has been necessary to maneuver the distal extremity of the catheter extensively and to reposition it radially incrementally in the chamber of the heart. Such a procedure has been found to be time consuming and relatively inaccurate. There is therefore a need for a new and improved endocardial mapping and ablation system and method for accomplishing the same.

OBJECTS OF THE INVENTION

In general it is an object of the present invention to provide an endocardial mapping and ablation system and a method which utilizes a large number of electrodes making it possible to perform endocardial mapping accurately and rapidly.

Another object of the invention is to provide a system and method of the above character in which ablation can be precisely carried out.

Another object of the invention is to provide a system and method of the above character in which bipolar electrode pairs are utilized.

Another object of the invention is to provide a system and method of the above character in which a plurality of radially and longitudinally spaced electrodes are provided which make possible simultaneous measurements through substantially 360° of a wall forming a chamber in the heart.

Another object of the invention is to provide a system and method of the above character in which the electrodes are expanded into engagement with the wall of the chamber of the heart and are maintained in engagement with that wall during pumping action of the heart.

Another object of the invention is to provide a system and method in which the electrodes are yieldably retained in engagement with the wall forming the chamber of the heart during the time that the heart is expanding and contracting the chamber.

Another object of the invention is to provide a system and method of the above character in which a catheter probe is utilized having an expandable distal extremity and in which the distal extremity of the catheter probe is adapted to be disposed in the chamber of the heart.

Another object of the invention is to provide a system and method of the above character in which the presence of the distal extremity of the probe in the heart does not substantially impede the flow of blood in the chamber of the heart.

Another object of the invention is to provide a system and method of the above character in which the mapping and ablation procedures can be carried out without movement of the distal extremity of the catheter probe with respect to the wall forming the chamber of the heart.

Additional objects and features of the invention will appear from the following description in which the preferred embodiment is set forth in detail in conjunction with the accompanying drawings.

BRIEF DESCRIPTION OF THE DRAWINGS

FIG. 2 is an enlarged plan view showing in particular the flexible sheet used to form the cylindrical member at the distal extremity of the catheter probe shown in FIG. 1.

FIG. 3 is an enlarged detail view of a portion of one of the arms of the cylindrical member showing the spring metal strip used in the arm.

FIG. 4 is an enlarged cross sectional view taken along the line 4—4 of FIG. 2.

FIG. 5 is an enlarged cross-sectional view taken along the line 5—5 of FIG. 2.

FIG. 6 is an enlarged detail view partially in cross section of the distal extremity of the catheter probe.

FIG. 7 is a cross-sectional view taken along the line 7—7 of FIG. 2.

FIG. 8 is an enlarged cross-sectional view taken along the line 8—8 of FIG. 2.

FIG. 9 is a cross-sectional view taken along the line 9—9 of FIG. 2.

FIG. 10 is a schematic diagram of the electronic circuitry utilized in the system for performing the method of the present invention.

FIG. 11 is a cross-sectional view of the heart showing the manner in which the system and catheter probe of the present invention are employed in the right ventricle to achieve mapping and/or ablation in accordance with the method of the present invention.

FIG. 12 is a cross-sectional view taken along the line 12—12 of FIG. 11.

FIG. 13 is a timing diagram for the circuitry shown in FIG. 10.

FIG. 14 is a partial view of another sheet incorporating the present invention for use with a catheter probe which shows a plurality of chips carried thereby.

FIG. 15 is a cross sectional view of a catheter probe showing the manner in which the plurality of chips shown in FIG. 14 are radially disposed about a mandrel for the catheter probe.

FIG. 16 is a partial plan view of another catheter probe incorporating the present invention and for use with the system and method of the present invention.

FIG. 17 is a cross sectional view taken along the line 17—17 of FIG. 16.

FIG. 18 is a cross sectional view taken along the line 18—18 of FIG. 17.

FIG. 19 is a partial elevational view showing the catheter probe of FIG. 16 with the expandable means in an expanded position.

FIG. 20 is a cross-sectional view taken along the line 20—20 of FIG. 19.

FIG. 21 is a plan view of an alternative bipolar electrode for use with the present invention.

FIG. 22 is a side elevational view of another embodiment of the endocardial mapping and/or ablation catheter probe of the present invention.

FIG. 23 is a cross-sectional view of the catheter probe of FIG. 22 taken along the line 23—23 of FIG. 22.

FIG. 24 is an enlarged side elevational view, partially sectioned, of the catheter probe of FIG. 22 taken along the line 24—24 of FIG. 22.

FIG. 25 is a cross-sectional view of the catheter probe of FIG. 22 taken along the line 25—25 of FIG. 22.

FIG. 26 is a cross-sectional view of the catheter probe of FIG. 22 taken along the line 26—26 of FIG. 22.

FIG. 27 is a cross-sectional view of the catheter probe of FIG. 22 taken along the line 27—27 of FIG. 26.

FIG. 28 is a cross-sectional view, partially cut away, of the catheter probe of FIG. 22 taken along the line 28—28 of FIG. 27.

FIG. 29 is a cross-sectional view of the heart showing the manner in which another embodiment of the endocardial mapping and/or ablation catheter probe of the present invention is employed in the right ventricle.

FIG. 30 is side elevational view of the distal extremity of the catheter probe of FIG. 29.

FIG. 35 is side elevational view, similar to FIG. 30, of the distal extremity of yet another embodiment of the endocardial mapping and/or ablation catheter probe of the present invention.

FIG. 36 is a cross-sectional view of the heart showing the manner in which still another embodiment of the endocardial mapping and/or ablation catheter probe of the present invention is employed in the right ventricle.

FIG. 37 is side elevational view of the distal extremity of the catheter probe of FIG. 36.

SUMMARY OF THE INVENTION

Figure 1:
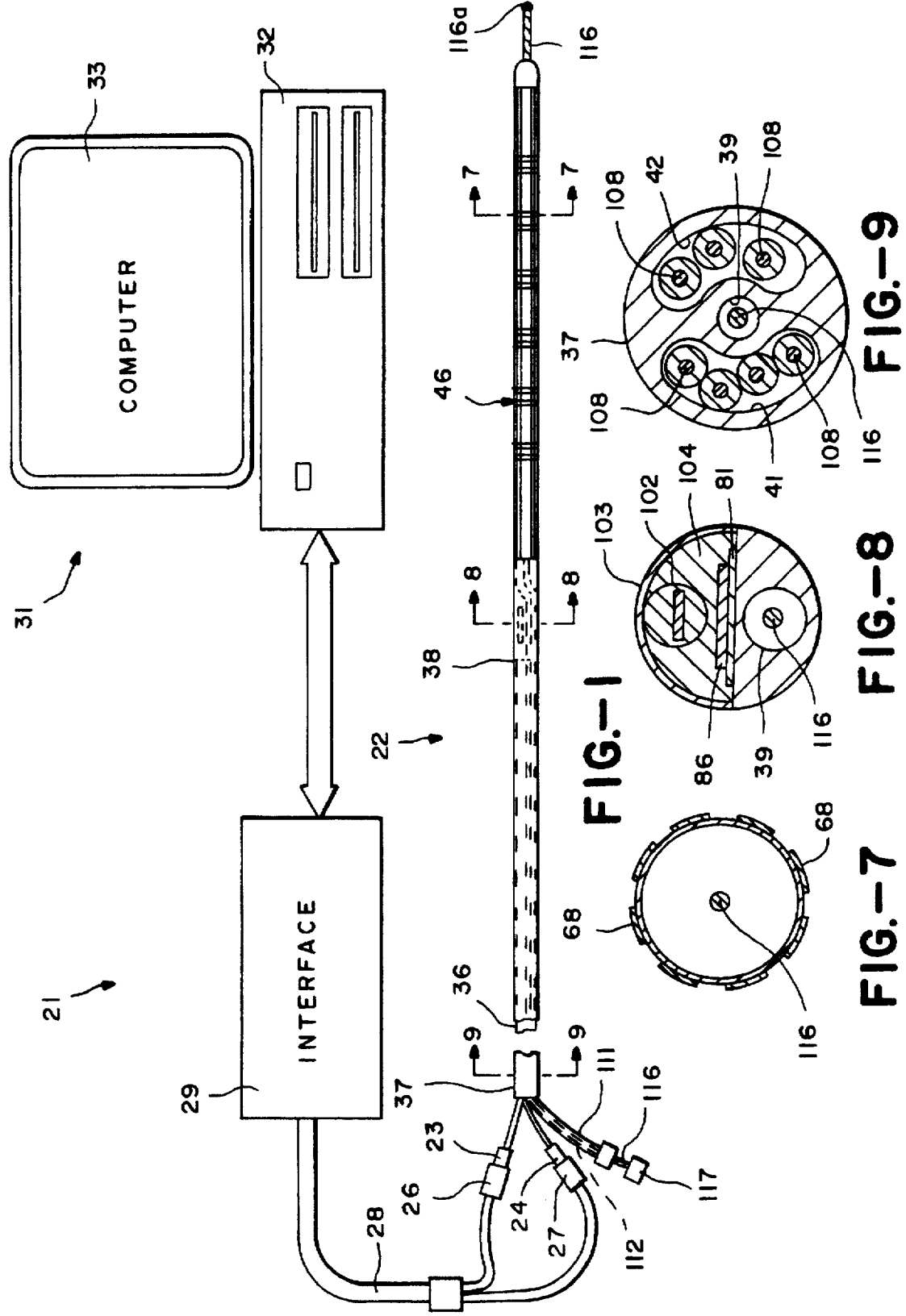
FIG. 1 is a schematic illustration of an endocardial mapping and ablation system end catheter probe incorporating the present invention.

In general, a catheter probe is provided comprising a flexible elongate tubular member having proximal and distal extremities. Expandable means capable of moving from a contracted position to an expanded position is secured to the distal extremity of the flexible elongate tubular member and is formed from at least two elongate members movable between contracted and expanded positions. The elongate members have extremities which are joined so that the elongate members extend at an angle relative to each other to form a vee therebetween. A plurality of longitudinally and radially spaced-apart electrodes are carried by the expandable means so that they can be moved into engagement with the wall of the heart when the expandable means is expanded into the expanded position. Electrical conductors extend through the elongate tubular member and are connected to the electrodes for performing electrical functions with respect to the electrodes. An elastomeric material is adhered to the joined extremities of the elongate members and is disposed within the vee for inhibiting the formation of thrombus on the elongate members while the expandable means is disposed within the blood of the heart.

DETAILED DESCRIPTION

More in particular, the endocardial mapping and ablation system 21 as shown in the drawings consists of a catheter probe 22 which is provided with a high voltage connector 23 and a signal connector 24 that are connected to mating connectors 26 and 27 forming a part of a cable 28. Cable 28 is connected to a catheter interface module 29 which supplies and receives appropriate signals to and from a computer 31 that is provided with a disc drive 32 and a monitor 33. It is also provided with a keyboard (not shown) for use in controlling the operation of the computer.

The catheter probe 22 consists of a flexible elongate tubular member 36 formed of a suitable material such as plastic which is circular in cross section as shown in FIG. 7. The tubular member 36 has a suitable diameter as for example 0.10" to 0.150" and a suitable length as for example from 100 to 150 cm. The tubular member 36 is provided with proximal and distal extremities 37 and 38 and is provided with at least one lumen and as shown in FIG. 9 is provided with three lumens 39, 41 and 42 in which lumen 39 is a centrally disposed lumen and lumens 41 and 42 are two generally crescent-shaped lumens provided on opposite sides of the lumen 39. Both lumens 39 and 41 extend from the proximal extremity 37 to the distal extremity 38 of the tubular member 36.

A flexible expandable cylindrical member 46 is secured in a fixed position to the distal extremity of the flexible elongate tubular member 36. The expandable cylindrical member 46 is movable between contracted and expanded positions as hereinafter described. The expandable cylindrical member is provided with a plurality of circumferentially spaced apart longitudinally extending flexible arms 47 having adjoined proximal and distal extremities or end portions 48 and 49 (see FIG. 6).

The flexible expendable cylindrical member is formed from a flexible flat sheet 51 (see FIG. 2) which is in the form of an elongate rectangle having sideways extending ears 52 and 53 on opposite ends. The sheet 51 is formed of a suitable insulating material such as plastic. One plastic found particularly suitable is a polyimide identified as Kapton (trademark). Assuming that the plurality of arms 47 to be utilized in the cylindrical member 46 is eight, the sheet 51 is slitted with a knife or die (not shown) to provide parallel spaced apart slits 56 extending longitudinally between the ears 52 and 53 to form the plurality of circumferentially spaced longitudinally extending arms 47. Small holes 57 are provided on the opposite ends of each of the slits 56 and serve to prevent propagation of the 56 slits into the proximal and distal extremities or end portions 48 and 49 of the sheet 51.

In order to impart springiness to the arms, the sheet 51 can be formed of two plastic sheets bonded together over die cut metal strips 61 of a suitable material such as stainless steel or plastic having narrowed portions 61a (see FIG. 3) so that the metal strips 61 are embedded between the two layers 62 and 63 of plastic (see FIG. 4) and encapsulated therein so that they lie in the areas between the lines in which the slits 56 are to be cut. In certain applications of the present invention, it may be desirable to form the strips 61 with a particular pattern to achieve a desired conformation for the bowing out of arms 47 of the expandable cylindrical member 46 when it is expanded as hereinafter described. The narrowed portion 61a can be provided at the proximal extremity to achieve greater bonging of the arm 47 in that region as the cylindrical member 46 is expanded as hereinafter described. The stainless steel strips can have a desired width, as for example, less than the width of the arms 47 and can have a suitable thickness as for example 0.001" to 0.010" in thickness and the plastic layers 62 and 63 can have a suitable thickness ranging from 0.001" to 0.010" in thickness and typically a thickness of 0.002".

Radially spaced apart rectangular radiopaque markers 64 formed of a suitable material such as lead or platinum can be positioned so that they underlie the stainless steel strips 61 and are embedded between the layers 62 and 63 of the layers 62, 63 and 64 forming the sheet 51. As shown in FIG. 2, the markers 65 are staggered in distance from the distal extremity so that they form a portion of a helix when the sheet 51 is formed into the cylindrical member 46 as hereinafter described. The markers 65 are only placed on certain of the arms 47 as for example five of the eight arms shown in FIG. 2. This aids in ascertaining the rotational position of the member 46 under fluoroscopy as hereinafter described.

A plurality of longitudinally end radially spaced apart sets 66 of bipolar electrodes 67 and 68 are provided on the exterior surfaces 69 of the arms 47 which serve as insulating substrates and are spaced laterally of sheet 51 (see FIG. 6) and circumferentially around the cylindrical member 46 (see FIG. 6). The cylindrical member 46 serves as an expandable means secured to the distal extremity of the tubular elongate element 36 and is movable between contracted and expanded positions whereby when the expandable means is moved to the expanded position the electrodes 67 and 68 are brought into engagement with the wall of the heart forming the chamber in which the expandable means is disposed as hereinafter described.

The electrodes 67 and 68 as shown are rectangular in shape and can have a length of 0.040" and a width of 0.040". The bipolar electrodes 67 and 68 can be separated by a suitable distance as for example 0.040". If desired the electrodes 67 and 68 can be of different sizes. Leads 71 are provided on the interior or inner surfaces 72 of the arms 47. The electrodes 67 and 68 and the leads 71 are formed of a suitable conductive materials. The outer or exterior surfaces 69 and the inner or interior surfaces 72 of the arm 47 of sheet or substrate 51 are coated with vapor deposited or electroplated layer of a suitable conductive metal such as copper to provide a copper layer 73 of a suitable thickness as for example 0.0005". The sheet 51 is then drilled to form holes 74 extending between the copper layers 73. Additional conductive material such as copper is then plated through the holes 74 to form the vies 76 (see FIG. 5). Thereafter, conventional etching techniques are used to remove the undesired copper material on the outer surfaces 69 and on the inner surfaces 72 of the arms 47 so that there remains longitudinally spaced apart electrodes 67 and 68 on the outer surface 69 and laterally spaced apart longitudinally extending leads 71 which are connected to the sets 66 of electrodes 67 and 68 by the vies 76. Each of the electrodes 67 and 68 is connected to one of the leads 71 by a via 76. The leads 71 are insulated from the metal strips 61 by the plastic layer 63.

The electrodes 67 and 68 as well as the leads 71 can be augmented by plating onto the copper layer 73. Thus, as shown in FIG. 5, the electrode 67 can be augmented by depositing a nickel layer 77 on the copper layer 73 followed by a gold layer 78 deposited on the nickel layer 77. Gold is particularly suitable as a final layer in this application because it is inactive in blood. It also is an excellent conductor.

The proximal end of the sheet 51 shown in FIG. 2 is provided with an extension 81. A multiplexer chip 86 of the type hereinafter described is mounted on or attached to extension 81 by conventional bonding techniques and is connected by conventional techniques to the leads 74 connected to the electrodes 67 and 68. In forming the sheet 51 of FIG. 2 into the cylindrical member 46, a distal mandrel 91 and a proximal mandrel 92 are utilized. The distal mandrel 91 is cylindrical in form and can be formed of a suitable material such as plastic or metal. The distal mandrel 91 is provided with a centrally disposed hole 93 which is provided with an outwardly flared portion 93a. The proximal mandrel 92 is also formed of a suitable material such as plastic and is provided with a cup-like recess 96 (see FIG. 6). It is also provided with a hole 97 which curves slightly downwardly to clear the recess 96 and extends through the mandrel 92. An additional hole 98 is provided in the mandrel 92 which opens into recess 96.

The sheet 51 is wrapped into a cylinder with the ears 52 overlapping the ears 53 by inserting the ears 52 through T-shaped slots 99 formed in the ears 53 and having pairs of spaced-apart slits 101 mating with the slots 99 so that the outer side margins of the sheet 51 are brought together to form another slit 56 between the two adjacent arms 47. The ears 52 and 53 also can be overlapped and fastened together on themselves by suitable means such as an adhesive. When fabricated in this manner, the cylindrical member 46 typically would have a diameter of approximately 0.150" and a suitable length as for example 2½" depending upon the size of the cavity in the heart to be mapped.

During wrapping of the ears 52 and 53 around the mandrel 91, the extension 81 and the chip 86 thereon is positioned within the cup-shaped recess 96. An encased crystal 102 is also mounted in the recess 96 overlying the chip 86. An RC oscillator (not shown) on the chip 86, may be used in place of crystal 102. The recess 96 is enclosed by semi-cylindrical cover 103. Prior to the placement of the cover 103, the chip 86 and the crystal 102 may be encapsulated in a suitable epoxy 104 placed in recess 96. The epoxy 104 can have heat sinking capabilities to dissipate any heat generated within the chip 86.

An alternative embodiment for the mounting of the multiplexer chip 86 is shown in FIGS. 14 and 15. As shown therein, the multiplexer chip 86 instead of being in only a single package as shown in FIGS. 2 and 6 can have its circuitry as well as other circuitry supplied in a plurality of chips, as for example, chips 86a, 86b and 86c which are mounted on the sheet 51 on the proximal end portion 49 immediately adjoining the ears 52 and the proximal extremities of the arms 47 so that the leads carried by the arms and connected to the electrodes 67 and 68 can be connected directly to the chips 86a, 86b and 86c. Chips 86a, 86b and 86c are spaced apart a suitable distance so that when the sheet 51 is wrapped about the proximal mandrel 92a shown in FIG. 15, the chips 86a, 86b and 86c are received within circumferentially spaced-apart recesses 96a, 96b and 96c provided in the proximal mandrel 92a. Such an arrangement has an advantage in that it makes it possible to provide additional circuitry if desired in the flexible elongate member 36 in close proximity to the electrodes 67 and 68. Also it permits the hole 97a (see FIG. 15) to be centrally disposed in the proximal mandrel 92a so that the pull wire 116 (hereinafter described) extending therethrough can extend along the center axis of the mandrel 92 rather than being offset as shown in FIG. 6.

A band 106 formed of a suitable conducting metal such as gold is provided at the distal extremity of the cylindrical member 46 over the mandrel 91 and serves as a ground. Alternatively, a large surface area electrode may be placed on the chest of the patient (not shown) to serve as a ground for the ablation current. A tubular sleeve 105 is fitted over the proximal mandrel 92 and extends over the proximal extremity of the cylindrical member 46. The sleeve 103 can be formed of a suitable material such as injection molded plastic. It can be formed as a separate sleeve or can be formed integral with the flexible elongate tubular member 36 forming the probe catheter 22 to provide a one-piece construction.

With respect to the embodiment shown in FIGS. 1–9, the tubular member 36 is rotationally aligned so that its central lumen 39 is in alignment with the hole 98 in the proximal mandrel 92. Because of the multiplexing capabilities of the chip 86 a relatively small number of wires or conductors 108 are connected to the chip 86. For example, as few as seven insulated conductors 108 can be provided which are bonded to pads (not shown) connected to the chip 86. The conductors 108 extend through the hole 98 and into the crescent-shaped lumens 41 and 47 provided in the flexible elongate member 36. The conductors 108 extend through the flexible elongate cylindrical member 36 and are connected to the connectors 23 and 24 heretofore described.

Seven conductors 108 would be provided when bipolar mapping and ablation is desired. Rather than using a single connector for all of the wires or conductors 108, it is desirable to separate the conductors into a high voltage set of conductors and a signal set of conductors. Thus, with seven conductors, the four conductors associated with high voltage can be connected into the quadrapole connector 23 and the three wires of the signal set can be connected into a biaxial connector 24.

Another tubular member 111 is connected to the proximal extremity 37 of the tubular member 36 and is provided with a lumen 112 which is in registration with the central lumen 39 provided in the tubular member 36. An elongate pull wire 116 is disposed in the lumens 112 and 39 and is formed of a suitable material such as stainless steel and can have a size as for example 0.014" in diameter. The pull wire 116 extends the length of the tubular member 36 and extends into the lumen 97 provided in the proximal mandrel 92 and then into the interior of the flexible expandable cylindrical member 46 which also may be called a cylindrical expandable electrode array and through the hole 93 provided in the distal mandrel 91. After the pull wire or element 116 has been inserted into the catheter and through the hole 93 of the mandrel 91, the distal extremity of the pull wire or element 116 is provided with an enlarged portion 116a which can be formed integral with the pull wire or element 116 or can be formed as a separate part bonded to the distal extremity of the pull wire. The portion 116a has a size which is sufficiently great so that it cannot be pulled through the hole 93 but which is still small enough to seat within the flared portion 93a of the hole 93 and not protrude substantially beyond the distal extremity of the mandrel 91. The pull wire 116 is provided with a knob 117 on its proximal extremity for operation of the pull wire.

Operation and use of the catheter or probe 22 in connection with the catheter interface module 29 and the computer 31 of the system 21 may now be briefly described as follows in utilizing the present invention. The catheter probe 22 is first used with the cylindrical expandable member or electrode array 46 in its normal contracted position which can be ensured by pushing on the knob 117 to fully extend the pull wire 116 to extend beyond the mandrel 91 so that it can serve as guide wire. The catheter or probe 22 is inserted into a cavity 131 of the heart 132 (FIG. 11) as for example the right ventricle of the heart in a human body by access through a femoral vein. This can be accomplished in a conventional manner by introducing the guide wire or pull wire or element 116 and thereafter the distal extremity of the catheter probe 22 into the femoral vein by the use of a guide sheath and/or a guiding catheter. This can be done in a conventional manner under fluoroscopy in which the catheter or probe 22 can be introduced through the superior inferior vena cave into the right atrium and then advanced into the right ventricle as shown particularly in FIGS. 11 and 12. In connection with this procedure, the pull wire 116 can be utilized as a guide wire and can be rotated by rotating the knob 117 to facilitate advancing the catheter through the desired path into the vessel lumen leading to the heart.

As soon as the distal extremity of the catheter probe 22 is positioned within the desired cavity of the heart as for example the right ventricle 131 of a heart 132 as shown in FIG. 11, connectors 23 and 24 can be interconnected with the mating connectors 26 and 27 so that the catheter probe 22 is connected to the catheter interface module 29 and the computer 31. Once this has been accomplished, the pull knob 117 can be retracted to move the portion 116a of the pull wire into the recess 93a and upon further pulling movement to cause expansion of the cylindrical expandable member or electrode array 46 to cause its arms 47 to be bowed outwardly as shown in FIG. 11 with the distal extremity or tip of the cylindrical electrode array 46 touching the distal extremity or apex of the right ventricle 131 so that the arms and the electrodes 67 and 68 carried thereby are brought into contact with the wall of the heart forming the right ventricle. As shown in FIG. 11, the bowing of the arms 47 is more pronounced at the proximal extremity 48 and at the distal extremity 49 of each of the arms 47. This increased bowing is made possible by providing the narrowed portions 61a on the proximal and distal extremities of the metal strips 61 as hereinbefore described. The flexibility of the arms 47 permits the heart to continue its normal beating pattern in moving the wall forming the right ventricle 131 inwardly and outwardly. At the same time because the arms 47 are spread or spaced apart as they are bowed outwardly, there is ample space between the arms so that normal blood flow in the right ventricle 131 can occur substantially unimpeded by the electrode array 46 when the array 46 is in the chamber. The springiness of the arms 47 is such that the arms 47 will yieldably follow the muscular contractions and expansions of the right ventricle and keep the bipolar electrodes 67 and 68 in substantially continuous contact with the heart wall and the electrical circuitry provided in the heart wall.

It should be appreciated that similar procedures can be used for positioning the catheter probe 22 in other chambers of the heart as for example the left ventricle of the heart.

In the embodiment shown in FIGS. 1–13, eight arms 47 are provided with six sets of electrode pairs with four of the arms having an additional sets of each end each for a total of 112 electrodes and 56 electrode pairs. Fewer bipolar pairs are provided at the ends because the arms 47 are closer together at the ends when the cylindrical expandable member 46 is expanded. Each bipolar electrode pair is connected to a differential amplifier 141 (see FIG. 10). Each of the differential amplifiers 141 is provided with input circuitry 142 which consists of current limiting resistors R1 and R2 connected to diodes D1 and D2 on opposite sides of the input line with the diode D2 being connected to ground and diode D1 being connected to a positive voltage. Diodes D3 and D4 are connected to the other input line with diode D4 being connected to ground and diode D3 being connected to the positive voltage. These serially connected diodes serve to protect the inputs to the amplifiers 141 during the time that ablation voltages are being applied as hereinafter described. The input circuitry has the capability of limiting the voltage rise at the inputs of the amplifier 141 to approximately ½ volt. The differential amplifiers 141 have a suitable gain as for example typically between 100 and 500. Since the endocardial signals that are received from the heart are of relatively high amplitude, a very high gain is not required from the amplifiers 141.

The outputs of the amplifiers 141 are connected by 56 lines 142 identified from 1 to 56 to an analog multiplexer 146. The multiplexer 146 can have a suitable number of inputs as for example 64 inputs as shown. Inputs 1–56 are connected to the cylindrical expandable member 46. Inputs 57–58 can be grounded as shown. Inputs 59–62 can be connected to a positive voltage supply and inputs 63–64 are connected to ground. One or two of these inputs can be utilized for providing a synchronization signal for demultiplexing as hereinafter described.

The multiplexer 146 is driven by a 6 bit binary counter 151 which is supplied with a clock frequency from an oscillator 152 that is controlled by crystal 153 of a suitable frequency as for example, 200 KHz. The 200 KHz oscillator frequency provides a five microsecond cycle length per channel as shown in the waveform. The counter 151 supplies an output 156 shown in FIG. 13 on six lines 157 to the multiplexer 146. The multiplexer 146 is provided with an output 158 which is controlled by the binary counter 151 so that the output from each of the amplifiers 141 appears on the line 158 for the five microsecond pulse length provided by oscillator 152. In the FIG. 13, waveform 156 shows information being received on 56 channels with each channel having a 5 microsecond duration followed by a synchronizing pulse 159 which is 20 microseconds wide to complete one cycle of the multiplexer of 320 microseconds followed by the next 320 microsecond cycle. This provides an effective sampling rate of about 3000 samples per second.

The output 158 is connected to a buffer amplifier 161 which provides its output on pin 3 of the connector 24. The other pins 1 and 2 of the connector 27 are connected to ground and a plus voltage respectively. The pins 1 and 2 in the connector 24 are connected to ground and a plus voltage respectively in the interface module 17.

Thus the power for the chip 86 is supplied from the interface module 17 through pins 1 and 2 of the connector 27. Pin 3 in the connector 14 receives the output signal from pin 3 of the connector 24 and supplies it through a line 164 to a demultiplexer 166. The demultiplexer 166 is provided with a plurality of output channels 167. Assuming there are 64 input channels in the multiplexer 146, there would be a corresponding number of output channels in the demultiplexer 166.

The information on the line 164 containing the synchronizing signal is also supplied through a capacitor C1 to a phase locked loop (PLL) 168 and is connected to an RC filter network 169 consisting of a resistor R5 an a capacitor C2 connected to ground. The PLL 168 is provided with an output line 172 and has provided thereon a reconstructed 200 Khz voltage controlled oscillator output which is supplied to a counter 173. The counter 173 is provided with a plurality of output lines 174 which are connected to the demultiplexer 166. The lines 174 are provided with frequencies ranging from 100 KHz to 3.125 KHz with the 3.125 KHz line 174 being connected to the phase lock loop 168 by a line 176 which serves to couple the VCO output to the phase lock loop. The use of the PLL allows the reconstruction of the 200 KHz clock, which is synchronized to the 200 KHz clock 152 in the catheter chip 86.

The demultiplexer 166 serves to demultiplex the information supplied from the multiplexer 146 and supplies it on the 56 channels 167 to circuitry 181 which includes sample and hold circuitry, filter circuitry and A-D converters to provide an output on lines 182 in the form of a signal which is supplied to the computer 31 and to the display monitor 33. The computer 31 is provided with software which has the capability of analyzing information being supplied to it by utilizing sampling techniques well known to those in the art. The computer 31 performs an analysis on the information and by use of propagation and delay time analysis identifies and isolates the area within the ventricle which may contain a re-entry pathway which may need to be ablated. This information is displayed on the screen of the monitor 33 so that it can be reviewed by the physician so that the physician can make a decision as to whether or not ablation is desirable.

Let it be assumed that re-entry pathway has been located and it is desired to ablate the same. After the mapping has been accomplished by use of the catheter or probe 22 as hereinbefore described, the same catheter or probe 22 while still in place within the ventricle may be used for accomplishing the ablation. The attending physician inputs the desired commands to the keyboard (not shown) connected to the computer 31 to give the command to proceed with an ablation. As soon as such a command is received by the computer 31, the computer 31 sends a channel number serially to pin 3 of the connector 26 which is connected to the corresponding pin 3 of the connector 23 in a serial to parallel shift register 186 which is disposed in the catheter probe 22. The shift register 186 supplies the channel number to the demultiplexer 186 on the six lines 187 to a high voltage demultiplexer 191. The shift register 186 is provided with a clocking signal on pin 4 of the connector 23 which is supplied with a clock signal on the corresponding pin 4 of the connector 26 from the computer 31.

The output of computer 31 is also connected to a high voltage ablation power supply 196 which is programmable as to channel number and to the amount of energy to be supplied on the channel and supplies its output to pins 1 and 2 of the connector 26 which is connected to corresponding pins 1 and 2 of the connector 23 which are connected to the demultiplexer 191. The high voltage demultiplexer 191 is provided with high voltage transistors which can tolerate the ablation voltages supplied by the power supply 196. Upon command, the ablation power supply 196 supplies a high voltage, high frequency (typically 50–100 volts at 750 KHz to 1 MKz) pulse across the pins 1 and 2 of connector 26. This high voltage pulse appears on the corresponding pins 1 and 2 of the connector 23 and is supplied by the demultiplexer 191 to the appropriate channel end appropriate electrode pair through lines 192 connected to the leads 74. This pulse appears across the electrode pair and causes an ablation to occur in the tissue of the wall of the right ventricle between the electrode pair. Alternatively, ablation can be accomplished between one of the electrode pairs and an external ground electrode placed on the chest of the patient. In this manner, it can be seen that a highly controlled ablation is provided which is precisely positioned with respect to the selected electrode pair.

Several milliseconds after the ablation pulse has been supplied to the appropriate electrode pair, mapping can again be resumed in the manner heretofore described to ascertain whether or not a re-entry pathway is still present. If the mapping indicates that at least a portion of the re-entry pathway is still present, high voltage pulses can be programmed by the computer end supplied to other appropriate electrode pairs until the re-entry pathway has been destroyed. From the pattern of the electrodes provided by the electrode array 46, it can be seen that a compact multiple electrode grid-like pattern is provided having electrode pairs precisely located throughout the entire surface of the wall of the heart forming the chamber in which the electrode array 46 is disposed so that ablation can be precisely controlled.

Programmed stimulation can be performed by using a selectable number of electrodes. In this mode of operation the interface 29 provides a programmable level of low voltage pulses (5-10 volts) via the high voltage line to stimulate the heart with synchronized pulses in order to induce or convert an arrythmia.

The staggered radiopaque markers 65 can be utilized to ascertain which of the arms 47 of the expandable member 46 is located closes to the anatomical point of interest in the heart cavity as for example the bundle of His. By observing this staggered relationship of the markers 65, the physician can select the signals coming from a specific arm 47 to analyze the same in the computer 31 to thereby ascertain the condition of the bundle of His.

The staggered relationship of the markers 65 also makes it possible for the attending physician to observe the amount of rotation which occurs in the expendable member 46 when it is rotated by rotation of the proximal extremity of the catheter probe 22. For example, since only five of the markers 65 are used on the right arm which are spaced circumferentially by 45° it is readily ascertainable whether rotating of 45° has occurred or more or less. If rotation of 45° has occurred, a marker 65 will be shifted to a different staggered position to the other side of the expandable member 46 which will be in registration with an arm 47. If rotation of less than 45° has occurred, the offset marker 65 will not be in alignment with one of the armks 47.

By providing an additional lumen in the catheter which is commonly accomplished in catheters and having that lumen open through a port into the right ventricle, it is possible to measure the pressure in the right ventricle during mapping or ablation. By measuring the pressure in the right ventricle, it is possible to ascertain when the ventricle is filled with blood or whether it is being squeezed. The timing of the ablation can be such that ablation occurs when the ventricle is squeezed to its smallest size. This may be desirable because at this point there will be the best contact between the electrode array 46 and the heart wall forming the ventricle. In addition, it is desirable to carry out the ablation at this point in time because at that time that the amount of blood in the ventricle is at a minimum. Thus, more of the energy created by the ablation pulse is dissipated into the heart wall rather than into the pool of blood in the right ventricle. Also, in order to accomplish this, a pressure transducer 201 can be provided in the cylindrical member or electrode array 46 and connected to electrical wires not shown into the multiplexer 146.

In accordance with the present invention, it can be seen that catheter probe 22 can be provided with an increased number of electrodes if desired. Additional channels can be readily provided in the multiplexer 146 and demultiplexer 166. The shape of the electrode array 46 can be made so that it conforms to the wall of the heart as it expands and contracts through the entire cardiac cycle. This is made possible because of the springiness of the individual arms 47 of the expandable member 46. Intimate contact is maintained with the wall of the heart minimizing the amount of energy which is dissipated into the blood pool within the cavity of the heart during ablation.

With the catheter, system and method of the present invention, mapping and ablation procedures can be carried out within relatively short periods of time, as for example, as little as one half hour. The construction of the catheter such that it will not interfere substantially with the cardiac output of the heart.

It should be appreciated that if desired, ablation can be accomplished with a separate catheter or device. It should also be obvious that if desired the system may be used to perform a routine electrophysiology study on a patient utilizing the programmed stimulation and mapping features of system.

Another embodiment of a catheter probe incorporating the present invention is shown in FIGS. 16–20. As shown therein, the catheter probe 211 which consists of a flexible elongate tubular member 36 very similar to the flexible elongate tubular member 36 hereinbefore described in the previous embodiment.

A plurality of longitudinally end radially spaced apart sets 216 of bipolar electrodes 217 and 218 are provided beyond the distal extremity of the flexible elongate tubular member 36. Expandable means is secured to the distal extremity of the flexible elongate tubular member 36 for carrying and supporting the sets 216 of electrodes 217 and 218. In the embodiment shown in FIGS. 16–20, the expandable means takes the form of a single flexible elongate strip or element 221 formed of a suitable material such as the plastic utilized for the arms 47 in the hereinbefore described embodiment of the present invention. The single flexible elongate strip 221 is utilized which is wrapped in a spiral fashion and is movable between contracted and expanded positions. The contracted position is shown in FIG. 16 and an expanded position is shown in FIG. 19.

The flexible elongate strip 221 is provided with an outer surface 222 and an inner surface 223. The sets of electrodes 216 can be formed as multilayer electrodes 217 and 218 on the outer surface 222 in the manner hereinbefore described for the previous embodiment and can have generally the same size and shape. Leads (not shown) can also be formed on the inner surface 223 in a manner similar to that hereinbefore described. The bipolar pairs of electrodes 217 and 218 are disposed longitudinally of the strip 221 or in other words in a helical direction as shown. If desired, the bipolar pairs of electrodes 217 and 218 can be arranged in different manners on the strip. For example, they can be staggered so that they extend in a direction which is at right angles to the longitudinal axis of the flexible elongate member 36.

It should be appreciated that if it is desired to achieve improved voltage propagation between the bipolar electrodes, a concentric arrangement of the bipolar electrodes can be utilized. As shown in FIG. 21, each set 226 of bipolar electrodes 227 and 228 has the electrode 227 is the form of a circular disc and electrode 228 as an annulus disposed coaxially with respect to the disc 227. The electrodes 227 and 228 can be multilayered as the electrodes 67 and 68 hereinbefore described. By way of example, the electrode 227 can have a diameter of 0.030", the space between the electrode 227 and the ring electrode 228 0.030" with the ring electrode 228 having a width of approximately 0.010". The sets 226 of electrodes 227 and 228 can be spaced lengthwise of the flexible elongate strip 221 so that they are spaced apart radially and longitudinally when the flexible elongate strip 221 is wrapped in the spiral manner shown in FIG. 16.

Means is provided for moving the expandable means expanded between expanded and contracted positions and consists of an elongate cylindrical tubular member 231 formed of a suitable material such as plastic having an annular recess 232 at the proximal extremity thereof, a plastic tube 233 formed of a heat-shrinkable material is shrunk over the proximal extremity of the tubular member 231 and is seated within the recess 232. It is also shrunk over the distal extremity of the mandrel 92 to secure the tubular member 231 to the mandrel 92. Another plastic or metal cylindrical tubular member 234 is provided in the form of a rounded tip. Cooperative means is provided for rotatably mounting the cylindrical tubular member 234 on the distal extremity of the cylindrical member 231 and consists of a female recess 236 formed in distal extremity of the cylindrical member 231 which is adapted to receive by a snap-in fit a male protrusion 237 on the tip member. Thus, it can be seen that there can be relative rotation between the cylindrical member 231 and the cylindrical member 234 while restraining longitudinal movement between the same. Means is provided for rotating the tip member 234 with respect to the distal extremity of the cylindrical member 231 and consists of a torque element or wire 246 which extends from the proximal extremity of the flexible elongate tubular member 36 through the hole 97 of the mandrel 92 and through a hole 247 in the cylindrical member 231 and is coupled to the tip member 234 by extending into a hole 248 in the tip member 234 and bonded therein by suitable means such as solder or an adhesive.

One of the ends of the flexible elongate strip 221 is secured to the distal extremity of the tip member 234 by suitable means such a band 251 and an adhesive. Similarly the other of the ends of the flexible elongate strip 221 is secured to the distal extremity of the mandrel 92 in a suitable manner such as clamping it under the cover 103. The torque wire 246 can be connected to the knob 117 hereinbefore described which can be utilized for rotating the torque wire 246 rather than controlling the pull wire as in the previous embodiment.

The flexible elongate strip 221 is wound on the tubular member 231 in a clockwise direction and is relatively tightly wrapped as shown in FIG. 16 to assume its contracted position. The flexible elongate strip 221 can be moved to an expanded position by rotation of the torque element or wire 246 and the tip member 234 secured thereto in a counter-clockwise direction to cause the turns of the helix of the flexible strip 221 to gradually expand in a circumferential direction to an expanded position simulating a position such as that shown in FIG. 19, that it would assume within a chamber of the heart and to move the electrodes 217 and 218 carried thereby into engagement with the wall forming the chamber of the heart in which the expandable means is disposed.

The leads (not shown) on the inner surface 223 are connected to a multiplexer chip 86 provided in the distal extremity of the flexible elongate member 36 in the same manner as heretobefore described in connection with the previous embodiment. The multiplexer 86 is connected by leads to the interface module 29 and to the computer 31 in the same manner as the previously described embodiment.

The catheter probe 211 of the embodiment shown in FIG. 16–20 can be readily introduced into a chamber of the heart in the same manner as the embodiment of the catheter probe hereinbefore described. As soon as the distal extremity of the catheter or probe 211 is positioned within the desired cavity of the heart, the knob 121 can be rotated in the appropriate direction to cause unwinding of the spirally wrapped flexible elongate strip 221 to cause it to progressively enlarge. Rotation is continued until the enlargement is sufficient to bring the electrodes 217 and 218 carried thereby into engagement with the wall of the heart forming the chamber in which the distal extremity of the catheter or probe 211 is disposed. By applying additional rotational forces to the knob 117, the size of the spiral formed by the flexible elongate strip 221 can be increased until all or substantially all of the electrodes carried by the strip 221 are moved into engagement with the wall. Since the strip 221 is flexible, the heart can continue its normal beating pattern in moving the wall forming the chamber inwardly and outwardly. At the same time, the spacing provided between the turns of the spiral formed by the flexible elongate strip 221 permits normal substantially unimpeded blood flow in the chamber in which the catheter probe 211 is located. The springiness of the flexible elongate strip 221 permits the flexible elongate element or strip 221 to follow the muscular contractions and expansions of the heart while still maintaining the electrodes in continuous contact with the heart wall and in contact with electrical circuitry provided within the heart wall.

When the desired potential measurements have been made which will give potentials extending around the 360° of the chamber, additional potential measurements can be made by partially contracting the spirally wound flexible elongate strips 221 by rotation of the knob 117 in an opposite direction the distal extremity of the probe 211 can be rotated through a desired angle, as for example, 15°. The flexible elongate strip 221 can then again be moved to an expanded position into engagement with the heart wall and additional potential measurements made.

If thereafter, it is desired to carry out an ablation step, this can be accomplished in the manner hereinbefore described by providing a high voltage between a selected set of bipolar electrodes.

Thereafter, after the desired procedures have been carried out, the catheter probe 211 can be removed from the body by operating the knob 117 to move the flexible elongate strip 221 into its contracted position helically wrapped about the tubular member 231. The entire catheter probe 211 can then be removed in a conventional manner.

It should be appreciated that rather than providing a single flexible elongate element or strip 221, a plurality of such flexible elements or strips can be provided which are disposed adjacent to each other to form a plurality of helices. The helices can be wound into a plurality of abutting or nearly abutting helices which can be expanded and contracted in the same manner as a single helix formed from a single flexible elongate member strip 221.

From the foregoing, it can be seen that several embodiments of the present invention have been provided which can be utilized for carrying out endocardial mapping and ablation. All of the embodiments make possible the making of simultaneous measurements at many portions of the wall forming the chamber of the heart in which the catheter probe is disposed, making it possible to make simultaneous potential measurements from such portions extending through 360°. Thus, it is possible to map the entire heart wall forming the chamber in a single step without the necessity of rotating the catheter probe to several rotational positions which may be very time consuming. In addition, with such different positions it may be difficult to precisely ascertain where the measurements were made in the chamber of the heart.

All of the embodiments of the invention have the advantage that during operation of the probe within the chamber, the heart can continue its normal operation with substantially unimpeded blood flow in the chamber because of the spacing provided between expandable means carrying the electrodes.

In connection with the use of the catheter probe of the present invention in vivo it has been found that the basket-like construction of the probe as for example as shown in FIG. 11 due to its complex geometry causes formation of thrombus on the flexible arms 47. In order to prevent or at least inhibit the formation of thrombus it has been found desirable to coat the distal extremity of the catheter probe and the basket-like or helix type construction with an anti-thrombogenic agent as for example heparin, hirudin and streptokinase containing coatings 261 (see FIG. 11) which are applied to the catheter probe prior to insertion of the catheter probe into the heart. It has been found that these anti-thrombogenic coatings prevent and at least inhibit the formation of thrombus on the arms. The coating 261 can be applied by dipping the basket assembly which can be of the type as shown in FIG. 11 or the helix type construction shown in FIG. 20 into a solution containing the anti-thrombogenic agent so that it will adhere to the exterior surface of the arms without interfering with the electrical contact being made by the electrodes carried by the arms. Such coatings 261 may be covalently bonded to the catheter probe by techniques well known to those skilled in the art to provide coatings of a few Angstroms in thickness. Such a coating after it has been applied can be cured in a suitable manner such as by air drying at room temperature.

It should be appreciated that other embodiments of the medical probe device of the present invention can be provided which include basket assemblies carrying means for reducing the formation of thrombus thereon. In this regard, a medical probe 281 is shown in FIGS. 22–28 which includes a flexible elongate tubular member or catheter shaft 282 made from any suitable material such as plastic and having proximal and distal extremities 282a and 282b. Catheter shaft 282 extends along a central longitudinal axis 283 and is provided with at least one lumen in the form of central passageway 286 extending between proximal and distal extremities 282a and 282b. Shaft 282 further includes a plurality of four longitudinally-extending additional lumens 287 spaced apart around passageway 286 (see FIG. 25).

An expandable means in the form of basket assembly 291 is carried by distal extremity 282b of catheter shaft 282. Basket assembly 291 is formed from a plurality of eight elongate members or arms 292 having proximal and distal extremities 292a and 292b and inner and outer surfaces 293 and 294. Basket assembly 291 is movable between a first or contracted position shown in dashed lines in FIG. 22, in which the basket assembly is adapted to pass through a vessel of the body into a chamber of the heart, and a second or expanded position shown in solid lines in FIG. 22, in which basket arms 292 bow outwardly so as to engage the inside of the wall of the heart. Arms 292 are circumferentially spaced apart about axis 283 at approximately 45° angles and, as shown in FIG. 22, spaces 296 are provided between arms 292 for permitting blood to flow through basket assembly 291 while it is in its expanded position in the heart.

A plurality of electrodes 297 are carried by basket assembly 291 in longitudinally and radially spaced-apart positions along the arm. More specifically, a plurality of eight electrodes 297 are carried by each arm 292 in longitudinally spaced-apart positions. The eight electrodes on each arm 292 are grouped in four pairs so as to provide a plurality of four longitudinally spaced-apart bipolar electrodes 298.

Each arm 292 is generally strip-like in conformation and is formed from a flexible elongate support member or strip 301 made from any suitable material such as metal (see FIGS. 23 and 24). More specifically, strip 301 can be made from a superelastic shape memory alloy such as Nitinol and be provided with a predetermined bowed shape. Strip 301 has a thickness of approximately 0.007 inch at its center and a reduced thickness of approximately 0.004 inch at its proximal extremity and 0.035 inch at its distal extremity. As illustrated in FIG. 23, each arm 292 further includes a flex strip 302 having electrical or lead means in the form of conductors or traces 303 made from copper or any other suitable conductive material adhered to each side thereof. Traces 303 are electrically connected to electrodes 297. An insulating layer 306 made from any suitable material such as polyimide extends longitudinally along each side of flex strip 302 and is adhered thereto by any suitable means such as an adhesive (not shown). Flex strip 302 with insulating layers 306 thereon extends in juxtaposition to metal strip 301 and is secured thereto by an encapsulating sleeve 307 made from polyethylene terephthalate (PET) or any other suitable material. The sleeve 307 is heat shrunk around flex strip 302, insulating layers 306 and metal strip 301.

Means is included within probe 281 for securing proximal extremities 292a of arms 292 in circumferentially spaced-apart positions about distal extremity 282b of catheter shaft 282 (see FIG. 24). In this regard, medical probe 281 is provided with a tubular inner bushing 308 made from a stainless steel hypotube or any other suitable material. Bushing 308 has proximal and distal extremities 308a and 308b. Proximal extremity 308a is press fit within the distal end of passageway 286 and is provided with a plurality of circumferentially-extending slots 311 therein for providing a mechanical lock between the bushing 308 and the soft plastic material of catheter shaft 282. Inner bushing 308 is further secured within catheter shaft 282 by an epoxy 312 disposed within slots 311 and engaging the inside of passageway 286. Intermediate and outer bushings 313 and 314, each made from a stainless steel hypotube or other suitable material, extend concentrically around distal extremity 308b of inner bushing 308. Arm proximal extremities 292a extend longitudinally along the outside of outer bushing 314. Metal strips 301 of arms 292 extend with an interference fit between bushings 308, 313 and 314 so as to secure arm proximal extremities 292a to catheter shaft 282. More specifically, the proximal ends of strips 301 for four of the arms 292 circumferentially spaced approximately 90° relative to each other extend between inner and intermediate bushings 308 and 313 while strips 301 for the other four arms extend between intermediate and outer bushings 313 and 314. In this manner, strips 301 of adjacent arms 292 alternate from extending between bushings 308 and 313 and bushings 313 and 314. An adhesive (not shown) is further provided between and around bushings 308, 313 and 314 for further securing the arms 292 to catheter shaft 282.

Flex strips 302 with traces 303 thereon extend longitudinally in a proximal direction from arm proximal extremities 282a as shown in FIG. 24. Lead or electrical means in the form of eight cables 316 extend through lumens 287 of catheter shaft 282, two cables 316 in each lumen 287 as illustrated in FIGS. 24 and 25. Each cable 316 includes a plurality of at least eight conductive filaments or conductors 317. The distal ends of cables 316 are respectively secured to the proximal ends of flex strips 302 and the conductors 317 of each such cable 316 are respectively connected to the traces 303 of each such flex strip 302. Nylon thread 321 extends circumferentially around the outside of flex strips 302 for binding them together and to inner bushing 308. An encapsulant made from any suitable material such as epoxy extends circumferentially around inner bushing 308 on both sides of the proximal ends of flex strips 302 and the distal ends of cables 316 secured thereto for providing a flexible body 322 which extends distally of catheter shaft 282 to proximal extremities 292a of arms 292. Inner bushing 308 provides rigidity to body 322 at the connection of traces 303 and conductors 317. Body 322 thus acts as a rigid insulator around the electrical connection of traces 303 and conductors 317 so as to minimize shorts therebetween and further secures arms 292 to distal extremity 282b of catheter shaft 282. Body 322 is relatively flexible as it extends distally of bushing 308 about arms 292. Cables 316 extend proximally through catheter shaft lumens 287 to a pin connector 323 secured to proximal extremity 282a of the catheter shaft 282. The pin connector 323 is electrically coupled to a controller 324 which includes a computer and a power supply for generating radio frequency energy.

Arms 292 extend distally of catheter shaft 282 so that adjacent arms 292 extend at an acute angle relative to each other. Arm distal extremities 292b are joined together as shown in FIGS. 26–28 so that adjacent distal extremities 292b meet at an acute angle relative to each other. First and second plate members 331 and 332 are provided and are disposed at a substantially right angle to central longitudinal axis 283 in juxtaposition to each other. Plate members 331 and 332 are secured together by any suitable means such as an adhesive (not shown) to form a disk 333 having a circumferentially-extending outer surface 334 and generally planar proximal and distal surfaces 336 and 337. Disk 333 has a diameter of approximately 0.11 inch and a thickness of approximately 0.006 inch. Disk 333 is provided with a plurality of four first slots 338 and a plurality of four second slots 339 extending between surfaces 336 and 337. Slots 338 and 339 each have a cross-sectional size and shape slightly larger than the cross-section of metal strips 301. Each of first and second slots 338 and 339 is disposed generally at a right angle to a radius of disk 333. First slots 338 are each spaced a distance of approximately 0.04 inch from the center of disk 333 and spaced around the disk 333 at approximately 90° intervals. Each of second slots 339 is spaced a distance of approximately 0.03 inch from the center of disk 333 so as to be disposed inside first slots 338. The second slots 339 are spaced apart around disk 333 at approximately 90° intervals and are angularly offset from first slots 338 by approximately 45° (see FIG. 28). Arm distal extremities 292b are each provided with a significant bend 346 so as to provide a distal stub 347 which extends through one of slots 338 or 339. Bends 346 are facilitated by the reduced thickness of metal strips 301 at their distal extremities. An enlarged tig weld 348 is provided on the end of each distal stub 347 for retaining the stubs 347 within slots 338 and 339. A thread 349 made from nylon or any other suitable material is wrapped and secured around stubs 347 between bends 346 and disk 333 for reasons discussed below.

Basket assembly 291 of medical probe 281 is provided with a soft tip 356 secured to the joined distal extremities 292b of arms 292 (see FIG. 27). Tip 356 is formed from any suitable elastomeric and soft material such as silicone 357 which generally encapsulates disk 333 and stubs 347. The tip 356 is provided with a rounded distal end 358. A spring 359 is attached to disk 333 and extends longitudinally from both surfaces 336 and 337 thereof for providing a secure connection between the silicone 357 and the disk 333. A central bore 361 extends through surfaces 336 and 337 of disk 333 for receiving spring 359. The internal diameter of bore 361 is slightly smaller than the external diameter of spring 359 so that when the spring 359 is screwed into the bore 361 a relatively rigid connection is provided therebetween. Tip 356 is formed by inverting basket assembly 291 and placing disk 333 within a mold after the disk has been brushed with a primer to enhance adhesion. The silicone 357 is then poured into the mold and allowed to dry. The silicone material 357 extends in and around spring 359. Thread 349 around stubs 347 precludes the portions of stubs 347 extending distally of disk 333 from puncturing the silicone material of tip 356 when basket assembly 291 is contracted.

Means is carried by basket assembly 291 for inhibiting the formation of thrombus thereon when the basket assembly is disposed within the chamber of the heart. In this regard, a suitable elastomeric potting compound or coating 366 such as tecoflex polyurethane encapsulates the silicone material 357 of tip 356 and, by doing so, is disposed within pocket or cavity 367 formed by silicone 357 on proximal surface 336 of disk 333 and distal extremities 292b of arms 292 (see FIGS. 26 and 27). Coating or fill 366 is formed so as to provide a smooth arcuate surface 368 which extends between inner surfaces 293 of arm distal extremities 292b when the arms 292 are in their expanded or bowed position. Fill 366 further provides a smooth transition between the silicone 357 on outer surface 334 of disk 333 and the outer surfaces 294 of arms 292.

The means of medical device 281 for reducing the formation of thrombus on basket assembly 291 further includes proximal and distal webbings 371 and 372 carried by the basket assembly 291 (see FIG. 22). Webbings 371 and 372 are made from any suitable elastomeric and durable material such as tecoflex polyurethane. Proximal extremities 292a of adjacent basket arms 292 come together to form a vee 373 therebetween. Similarly, distal extremities 292b of adjacent arms 292 come together at disk 333 to form a vee 374 therebetween. Thus, a plurality of eight proximal vees 373 and eight distal vees 374 are provided by basket assembly 291. A webbing 371 is formed in each proximal vee 373 and includes a concave arcuate surface 378 which extends between the adjacent arms 292. Similarly, a webbing 372 is disposed within each distal vee 374 and is formed with a concave arcuate surface 379 which extends between adjacent arms. Webbings 371 and 372 are preferably sized so that the distance between the center of respective arcuate surface 378 or 379 and the bottom of respective vee 373 or 374 ranges from approximately 0.010 to 0.050 inch. The webbings 371 and 372 have a thickness not greater than approximately 0.010 inch. The material of webbings 371 and 372 is more flexible than the material of tip 356 so as to permit the expansion and contraction of basket assembly 291 as discussed above. Webbings 371 and 372 each have a thickness of not greater than 0.01 inch.

The distal extremity of catheter probe 281 and the basket assembly 291 is coated with an anti-thrombogenic agent as for example heparin, hirudin and streptokinase containing coatings 381 prior to insertion of the catheter probe into the heart for further inhibiting the formation of thrombus thereon (see FIG. 23). Coating 381 is applied to probe 283 prior to its insertion into the heart and the coating adheres to the exterior surface of the probe without interfering with the electrical contacts being made by electrodes 297. The coating 381 has a thickness ranging from a few Angstroms to approximately 0.001 inch.

The operation and use of medical probe 281 is similar to the operation and use of the medical probes discussed above. Bipolar electrodes 298 carried by basket assembly 291 can be used for sensing electrical signals from the wall of the heart so as to locate the origin of an arrhythmia. For example, basket assembly can be introduced by an introducer catheter (not shown) through a vessel of the body into the right ventricle of the heart. Once the basket assembly 291 is within the ventricle and tip 356 is engaging the apex of the ventricle, the introducer catheter is retracted relative to medical probe 281 so as to permit arms 292 to bow outwardly and basket assembly 291 to move to its expanded position. The reduced thicknesses at the proximal and distal extremities of metal strips 301 inhibit the arms 292 from buckling in the center while engaging the heart wall. The bowing of arms 282 causes electrodes 297 carried thereby to engage the wall of the heart. Signals from the endocardium are detected by bipolar electrodes 298 and transmitted via pin connector 323 to controller 324 which generates a map of the endocardium for facilitating location of the arrhythmia. Should it be desirable to ablate the endocardium, radio frequency energy can be supplied by controller 324 to one or more of electrodes 297 for creating lesions in the endocardium. It should also be appreciated that medical probe 281 can be used solely for detecting electrical signals from the endocardium and be within the scope of the present invention. In this case, any ablation of the heart wall can be performed by a separate catheter introduced into the ventricle through open probe passageway 286 or otherwise.

When basket assembly 291 is so disposed within the right ventricle or other chamber of the heart, soft tip 356 serves to provide an atraumatic contact point for deploying and holding basket assembly 291 at the apex of the ventricle. The soft silicone material of tip 356 inhibits the creation of trauma at the ventricle apex during operation of basket assembly 291.

The construction of medical probe 281 minimizes if not eliminates the formation of thrombus on the basket assembly 291 by eliminating acute angles and smoothing out edges at the joined proximal extremities 292a and joined distal extremities 292b of arms 292. Distal fill 366 inhibits blood from clotting within cavity 367 at the distal extremity of basket assembly 291 by minimizing areas around cavity 367 where blood can stagnate and thus coagulate. In a similar manner, proximal and distal webbings 371 and 372 inhibit thrombus from forming at the proximal and distal extremities of arms 292, specifically within proximal and distal vees 373 and 374.

Although medical probe 281 has been illustrated and described as having webbings provided at the proximal and distal extremities of basket assembly 291, it should be appreciated that a basket assembly having such webbing between adjacent arms at only its distal extremity can be provided and be within the scope of the present invention. Alternatively, a basket assembly can also be provided in which webbing is provided only at the proximal extremity between adjacent arms. Furthermore, it should be appreciated that webbing could be provided only between certain arms or between other adjoining members of an expandable means and be within the scope of the present invention.

Figure 32:
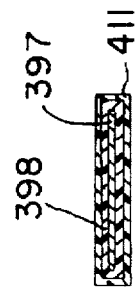
FIG. 32 is a cross-sectional view of the catheter probe of FIG. 29 taken along the line 32—32 of FIG. 31.

In another embodiment of the invention, a catheter probe 391 is provided which is similar in many respects to catheter probe 281. The proximal extremity of probe 391 is identical to the proximal extremity of probe 281. The distal extremity of probe 391 is illustrated in FIGS. 29–32 where like reference numerals are used to identify like components of probes 281 and 391. Catheter probe 391 includes an expandable means in the form of asymmetric basket assembly 392 secured to distal extremity 282b of torquable catheter shaft 282. Basket assembly 392 is formed from a plurality of eight arms. More specifically, the basket assembly 392 includes at least one and as shown two support arms 393 having proximal and distal extremities 393a and 393b and between three and six and as illustrated six mapping arms 396 having proximal and distal extremities 396a and 396b and a central portion 396c intermediate extremities 396a and 396b. As shown more clearly in FIG. 31, arms 393 and 396 are spaced around central longitudinal axis 283 with mapping arms 396 extending along one side of axis 283 and support arms 393 being aligned about the axis 283 generally opposite to the mapping arms 396. Mapping arms 396 are spaced relatively closely together and subtend an angle of less than 180° and as shown approximately 120° about longitudinal axis 283. The mapping arms 396 would preferably subtend an angle about axis 283 of approximately 90° for a basket assembly similar to basket assembly 392 but having only five mapping arms 396. Each arm 396 is spaced apart a distance ranging from approximately 0.2 to 0.6 inch at the longitudinal center of basket assembly 392, while support arms 393 are spaced apart a distance of approximately 0.4 to 2.4 inches at this point. Mapping arms 396 are substantially similar in construction to the arms 292 of medical probe 281. Support arms 393, as illustrated in FIG. 32, include only a flexible metal strip 397, substantially similar to metal strip 301, encapsulated by an insulating sleeve 398 substantially similar to sleeve 307.

Basket assembly 392 further includes an atraumatic tip 401 substantially similar to tip 356. Arm proximal extremities 393a and 396a are secured to distal extremity 282b of catheter shaft 282 in the same manner in which arm proximal extremities 292a of medical probe 281 are secured to catheter shaft distal extremity 282b thereof. Arm distal extremities 393b and 396b are secured to tip 401 in substantially the same manner in which arm distal extremities 282b are secured to tip 356 of medical probe 281. As so formed, basket assembly 392 is movable between contracted and expanded positions in the same manner as basket assembly 291 of medical probe 281. When in its expanded position, basket assembly 392 has a length ranging from approximately 1.5 to 3.0 inches so as to extend substantially the entire length of the chamber of the heart, as shown in FIG. 29 with respect to the right ventricle, and a diameter ranging from approximately 2.5 to 4 inches at its longitudinal midpoint.

A plurality of electrodes 402 are carried by mapping arms 396 for permitting high density mapping of regions of the endocardium. As shown in FIG. 30, a plurality of eight electrodes 402 are provided on the mapping region or sector of each mapping arm 396. These electrodes are disposed in pairs so as to form four bipolar electrodes 403 longitudinally spaced apart along the length of the arm 396.

Catheter probe 391 includes means for inhibiting the formation of thrombus thereon. In this regard, proximal webbings 404 substantially similar to proximal webbings 371 are provided in the crevices or vees 406 between adjacent arm proximal extremities 393a and 396a and distal webbings 407 substantially similar to distal webbings 372 are provided in the vees 408 formed by adjacent arm distal extremities 393b and 396b. Since the angle between adjacent mapping arms 396 is more severe and acute than the angles between arms 292 of basket assembly 291, webbings 404 and 407 extend longitudinally a distance of up to approximately 0.4 inch from the bottom of the respective vee 406 or 408. Distal fill 409 substantially similar to fill 366 described above is provided on the underside of tip 401. In addition, the distal extremity of catheter probe 391 and basket assembly 392 can be dipped or otherwise coated with an anti-thrombogenic coating 411 substantially similar to coating 381 described above.

In operation and use, asymmetric basket assembly 392 is introduced into a chamber of the heart such as the right ventricle 412 of the heart extending below valve 413 and formed by heart wall 414 in the same manner as discussed above with respect to basket assembly 291 of medical probe 281. Once within ventricle 412, basket assembly 392 is permitted to expand so that support and mapping arms 393 and 396 engage the wall of the heart. Since basket assembly 392 is generally wider than the ventricle, support arms 393 serve to urge mapping arms 396 against a portion of the heart wall so as to stabilize the basket assembly within the ventricle and provide good contact between electrodes 402 and the endocardium. The relatively close spacing between mapping arms 396 and the bipolar electrodes 403 carried thereby permit a high density map to be created from the electrical signals detected by electrodes 402. It should be appreciated that the spacing between mapping arms 396 contributes to the density of the map permitted by the basket assembly. As such, the number of mapping arms can be increased and/or the spacing between mapping arms decreased for creating higher density maps. Furthermore, a greater number of electrodes 401, for example sixteen, can be provided on each mapping arm 396 for further enhancing the definition of the endocardial map created by medical apparatus or probe 391.

The positioning of the electrodes 402 along the full length of arms 396 permits high density mapping of a "longitude" of the endocardium. Should mapping of another longitudinal portion of the endocardium be desired, basket assembly 392 can be contracted in a manner discussed above and rotated to another position before being expanded again for engaging the heart wall at this other longitudinal portion.

Webbings 404 and 407 and coating 411 are particularly desirable in basket assembly 392 because of the small angles created between mapping arms 396 where they join at tip 401 and at catheter shaft distal extremity 282b. It should be appreciated, however, that an asymmetric basket assembly 392 without webbings 404 and 407, distal fill 409 and/or coating 411 can be provided and be within the scope of the present invention. Furthermore, although electrodes 402 have been described as being arranged in the mapping sector of basket assembly 392 so as to create bipolar electrodes 403, it should be appreciated that unipolar electrodes can be provided on each mapping arm 396 and be within the scope of the present invention. It is preferable that the electrodes 402 in the mapping sector be arranged so as to be radially and longitudinally spaced apart a distance ranging from approximately 0.2 to 0.4 inch.

Electrodes 402 can be used for ablating the endocardium or a separate ablation electrode can be introduced into the chamber through central passageway 286 of catheter shaft 282 or otherwise.

Figure 33:
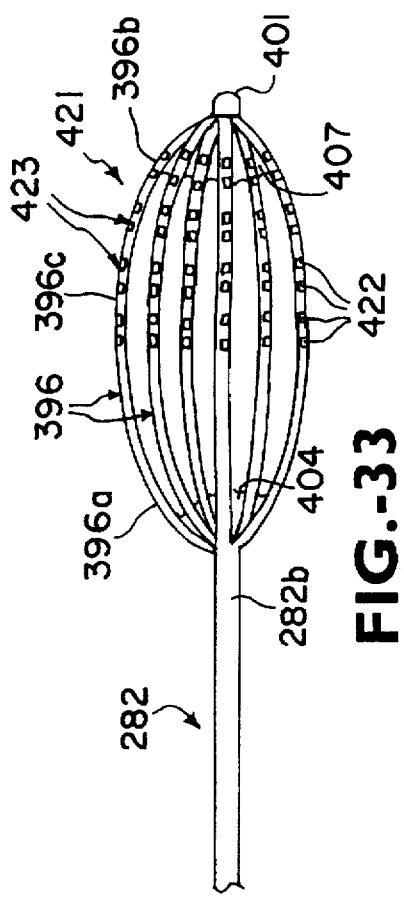
FIG. 33 is side elevational view, similar to FIG. 30, of the distal extremity of another embodiment of the endocardial mapping and/or ablation catheter probe of the present invention.
Figure 31:
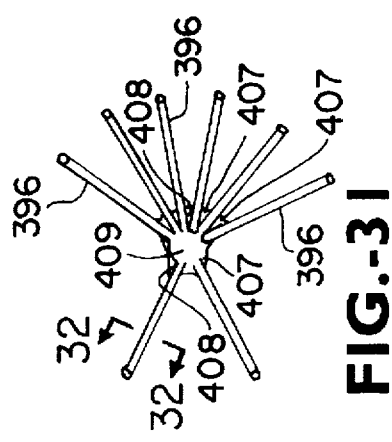
FIG. 31 is a cross-sectional view of the catheter probe of FIG. 29 taken along the line 31—31 of FIG. 30.
Figure 34:
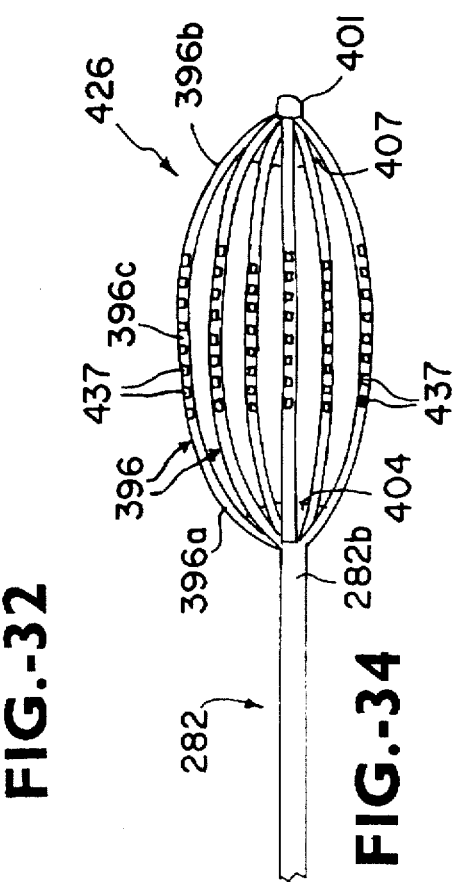
FIG. 34 is side elevational view, similar to FIG. 30, of the distal extremity of a further embodiment of the endocardial mapping and/or ablation catheter probe of the present invention.

Asymmetric basket assemblies substantially similar to basket assembly 392 can be provided with other arrays or patterns of mapping electrodes thereon. For example, a basket assembly 421 substantially similar in size, shape and construction to basket assembly 392 and secured to distal extremity 282b of catheter shaft 282 is shown in FIG. 33. Like reference numerals are used in describing like components of basket assemblies 421 and 392. A plurality of eight electrodes 422 arranged in four pairs of closely spaced-apart bipolar electrodes 423 are disposed on distal extremity 396b of each mapping arm 396. In another embodiment of an asymmetric basket assembly, basket assembly 426 substantially similar in size, shape and construction to basket assembly 392 and secured to distal extremity 282b of catheter shaft 282 is shown in FIG. 34. Like reference numerals are again used in identifying like components between basket assemblies 426 and 392. Basket assembly 426 includes a plurality of eight unipolar electrodes 427 longitudinally spaced apart at equal intervals on central portion 396c in relatively close spaced-apart positions. The electrodes 427 on adjacent arms are longitudinally offset relative to each other. In yet a further embodiment, an asymmetric basket assembly 431 substantially similar in size, shape and construction to basket assembly 392 and secured to distal extremity 282b of catheter shaft 282 is shown in FIG. 35. Again, like reference numerals have been used to describe like components between basket assemblies 431 and 392. In basket assembly 431, a plurality of closely spaced-apart mapping electrodes are carried by proximal extremities 396a of each mapping arm 396. More specifically, a plurality of eight electrodes 432 grouped in pairs of four bipolar electrodes 433 are carried by each arm proximal extremity 396a. It should be appreciated that more than eight electrodes can be provided on each mapping arm of basket assemblies 421, 426 and 431 and be within the scope of the present invention.

In operation and use, basket assemblies 421, 426 and 431 can be introduced into ventricle 412 or another chamber of the heart in substantially the same manner as basket assembly 392 for permitting high density mapping and/or ablation of a portion of the endocardium. Basket assemblies 421, 426 and 431 differ from basket assembly 392 in that they provide a higher density of electrodes 402 in a particular sector on mapping arms 396 so as to permit a more complete map of a particular region of the heart wall. The offset configuration of basket assembly 426 is advantageous as it minimizes zones between electrodes where information cannot be detected, for example, in the center of a square having corners defined by four nonoffset electrodes. As such, basket assembly 426 can provide a map with greater detail.

Figure 38:
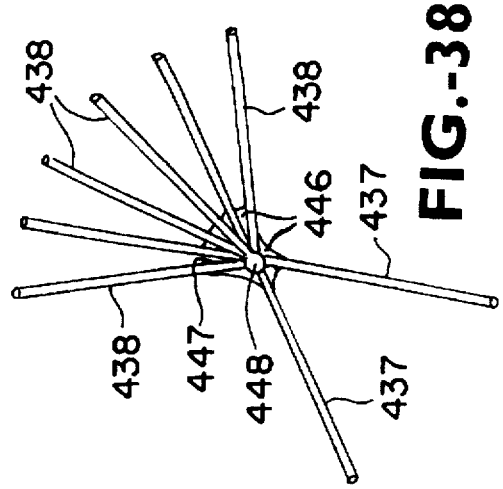
FIG. 38 is a cross-sectional view of the catheter probe of FIG. 36 taken along the line 38—38 of FIG. 37.

The asymmetric basket assembly previously described can have other conformations and be within the scope of the present invention. In this regard, a basket assembly 434 substantially similar to basket assembly 392 and secured to distal extremity 282b of torquable catheter shaft 282 in the same manner as discussed above is illustrated in FIGS. 36–38. Like reference numerals are used to describe like components of basket assemblies 434 and 392. Basket assembly 434 extends along central longitudinal axis 436 and includes at least one and as illustrated a plurality of two support arms 437 having proximal and distal extremities 437a and 437b. The basket assembly 434 also includes six mapping arms 438 having proximal and distal extremities 438a and 438b and a central portion 438c between extremities 438a and 438b. Arms 437 and 438 have the same respective construction of support and mapping arms 393 and 396 of basket assembly 392 and are secured at their proximal extremities to catheter shaft distal extremity 282b and at their distal extremities to an atraumatic tip 439 substantially similar to tip 401. Support and mapping arms 437 and 438 are aligned relatively opposite to each other about longitudinal axis 436. More specifically, mapping arms 438 subtend an angle about axis 436 of less than 180° and more specifically approximately 90°. As such, arms 438 are spaced apart a distance ranging from approximately 0.4 to 0.6 inch at their point of widest separation. Basket assembly 434 further includes an atraumatic tip 401 and is movable between contracted and expanded positions in the same manner as basket assembly 291.

When in its expanded position, as shown in FIGS. 36 and 37, basket assembly 434 has a length ranging from 0.5 to 1.6 inches so as to be substantially shorter than the longitudinal dimension of the heart chamber in which it is utilized. Basket assembly 434 has a diameter at its widest point ranging from 2.0 to 3.5 inches when in its expanded position and is thus provided with a transverse dimension which is greater than the widest point of the heart chamber in which it is to be introduced. This short and wide configuration of basket assembly 434 is permitted by metal strip 301 provided within each mapping arm 438 and the similar metal strip 397 provided within each support arms 437. As discussed above, strips 301 and 397 are made from any suitable flexible material such as superelastic Nitinol and are formed with a bowed shape corresponding to that of the expanded basket assembly 434. The strips 301 and 397 can be deformed, however, so as to permit basket assembly 434 to assume a contracted position similar to the contracted position shown in FIG. 22 with respect to basket assembly 291 for introducing the basket assembly into the heart.

A plurality of electrodes 441 are carried by mapping arms 438. These electrodes 441 are preferably disposed on central portion 438c of the mapping arms 438 in a manner similar to electrodes 427 of basket assembly 426 shown in FIG. 34. More specifically, a plurality of at least eight electrodes 441 are provided on each mapping arm 438. These electrodes 441 are arranged in pairs of four bipolar electrodes 442 which are spaced relatively closely together on arm central portions 396c.

Basket assembly 434 includes means for inhibiting the formation of thrombus thereon. This means includes proximal webbings 443 substantially similar to proximal webbings 404 described above and disposed within the vees 444 formed where adjacent arm proximal extremities 437a and/or 438a come together. Distal webbings 446 substantially similar to distal webbings 407 described above are provided in the vees 447 created where adjacent arms distal extremities 437b and/or 438b come together at tip 439. A fill 448 substantially similar to fill 366 is provided on the underside of tip 439 for providing a smooth transition between the distal extremities of arms 437 and 438. In addition, a coating 451 substantially similar to coating 381 is provided on the distal extremity of the catheter probe and on basket assembly 434. A portion of coating 451 is shown in FIG. 37.

In operation and use, basket assembly 434 is introduced into a chamber of the heart such as right ventricle 412 in substantially the same manner as discussed above with respect to basket assembly 291 of medical probe 281. Unlike the previously described basket assemblies, however, basket assembly 434 does not extend substantially along the full length of the ventricle. Instead, basket assembly 434 can be positioned longitudinally at a desired location or latitude in the ventricle before being permitted to expand outwardly to its oblong configuration. Once so expanded, support arms 437 urge bipolar electrodes 442 carried by mapping arms 438 against a portion of the endocardium. The relatively close spacing between mapping arms 438 and the relatively high density of electrodes 441 carried on central portions 438c thereof permit a high density map to be created from the electrical impulses detected by the electrodes.

Should it be desirable to obtain high density maps of other regions within the ventricle or chamber of the heart, basket assembly 434 can be contracted and moved to this other location. In this regard, the basket assembly 434 can be rotated about its longitudinal axis for permitting sensing of other circumferential regions at this same longitudinal position in the chamber. In addition, basket assembly 434 can be moved upwardly or downwardly within the chamber for permitting sensing of electrical impulses at other longitudinal regions of the chamber.

Basket assembly 434 is particularly desirable as it permits high density mapping with a single catheter at a significant number of longitudinal and circumferential positions within a chamber of the heart. Webbings 443 and 446, fill 448 and coating 451 inhibit blood within the heart from clotting at the vees, cavities and other possible points on basket assembly 434 where blood may tend to stagnate.

It has also been found that a relatively short and fat basket assembly such as basket assembly 434 is advantageous because it can accommodate a greater variety of heart chamber sizes. For example, when basket assembly 434 is disposed in a chamber which is transversely sized smaller than basket assembly 434, the inward compression of arms 437 and 438 merely causes the basket assembly to extend longitudinally within the chamber.

From the foregoing, it can be seen that a new and improved medical probe device has been provided with a basket assembly which inhibits the formation of thrombus thereon. Elastomeric material has been disposed on the basket assembly at locations where blood would tend to coagulate while the basket assembly is within the heart. A webbing has been provided between adjacent arms at the proximal and/or distal extremities of the basket assembly. The basket assembly has an atraumatic tip which inhibits the creation of trauma when the basket assembly is urged against the apex of a chamber within the heart. In addition, an asymmetrical basket assembly has been provided wherein certain of the arms are grouped closely together so as to permit high density of regions within the heart. The asymmetrical basket assembly can be sized to fill substantially the entire chamber of a heart. Alternatively, the asymmetrical basket assembly can be sized to fill less than the entire chamber of the heart so as to permit the basket assembly to be moved longitudinally to different positions within the chamber. A plurality of mapping electrodes are carried by the asymmetric basket assembly and can be located at various positions on the group of mapping arms thereof.

What is claimed is:

1. A mapping probe for introduction through a lumen into a chamber of a heart having blood therein and formed by a wall comprising a flexible elongate tubular member having proximal and distal extremities, expandable means movable from a contracted position to an expanded position secured to the distal extremity of the flexible elongate tubular member and formed from at least two elongate members, each of the elongate members having an extremity, means for joining together the extremities so that the elongate members extend at an angle relative to each other to form a vee therebetween when the expandable means is in the expanded position, a plurality of spaced-apart electrodes carried by the expandable means for engaging the wall of the heart when the expandable means is in the expanded position, electrical means extending through the flexible elongate tubular member and connected to the electrodes for performing electrical functions with respect to the electrodes and web-like means made of an elastomeric material adhered to the extremities of the elongate members and extending between the extremities within the vee for inhibiting the formation of thrombus in the vee when the expandable means is disposed within the blood of the heart.

2. A probe as in claim 1 wherein the web-like means is substantially planar in conformation.

3. A probe as in claim 1 wherein the elastomeric material is polyurethane.

4. A probe as in claim 1 wherein the elongate members are arms and wherein the extremities are the distal extremities of the arms.

5. A probe as in claim 4 wherein the arms extend at an acute angle relative to each other.

6. A probe as in claim 1 wherein the expandable means is a basket-like assembly having a plurality of longitudinally-extending spaced-apart elongate arms having joined proximal and distal extremities, the joined distal extremities of an adjacent pair of arms forming the vee.

7. A probe as in claim 6 wherein the elongate arms include a group of arms which are spaced relatively closely together and at least one support arm aligned generally opposite the group of arms, the plurality of electrodes being carried in longitudinally spaced-apart positions on the group of arms and the at least one support arm serving to urge the group of arms against the wall of the heart so as to permit high density mapping of the wall from electrical signals sensed by the electrodes.

8. A probe as in claim 1 together with an antithrombogenic agent disposed on the expandable means for inhibiting the formation of thrombus on the expandable means when the expandable means is disposed within the blood of the heart.

9. A mapping probe for introduction through a lumen into a chamber of a heart having blood therein and formed by a wall comprising a flexible elongate tubular member having proximal and distal extremities and at least one lumen extending therethrough, a basket assembly movable between contracted and expanded positions, the basket assembly having a plurality of longitudinally-extending circumferentially spaced-apart arms with proximal and distal extremities, means for joining the proximal extremities of the arms to the distal extremity of the flexible elongate tubular member, means for joining together the distal extremities of the arms so that the distal extremities of adjacent arms extend at an angle relative to each other to form a vee therebetween when the basket assembly is in the expanded position, a plurality of longitudinally spaced-apart electrodes carried by each arm for engaging the wall of the heart when the basket assembly is in the expanded position, electrical means extending through the flexible elongate tubular member and connected to the electrodes for performing electrical functions with respect to the electrodes and web-like means made of an elastomeric material extending within the vees between the distal extremities of the arms for inhibiting the formation of thrombus in the vees when the basket assembly is disposed within the blood of the heart.

10. A probe as in claim 9 wherein the means for joining the proximal extremities of the arms to the distal extremity of the flexible elongate tubular member includes means for joining together the proximal extremities of the arms so that the proximal extremities of adjacent arms extend at an angle relative to each other to form a vee therebetween when the basket assembly is in the expanded position, additional web-like means made from an elastomeric material extending within the vees between the proximal extremities of adjacent arms for inhibiting the formation of thrombus in said vees when the basket assembly is disposed within the blood of the heart.

11. A probe as in claim 10 together with an antithrombogenic agent disposed on the basket assembly.

12. A probe as in claim 9 wherein the web-like means is bendable to permit the distal extremities of the arms to move close together when the basket assembly moves to the contracted position.

13. A mapping probe for introduction through a lumen into a chamber of a heart having blood therein and formed by a wall comprising a flexible elongate tubular member having proximal and distal extremities, a sector-shaped basket movable between contracted and expanded positions, the sector-shaped basket having a plurality in excess of three longitudinally-extending spaced-apart arms lying within an angle of 180° or less about the longitudinal axis, the arms of the sector-shaped basket having proximal and distal extremities and a plurality of longitudinally spaced-apart electrodes, at least one additional arm extending along the longitudinal axis and having proximal and distal extremities, means for securing the proximal extremities of the arms to the distal extremity of the flexible elongate tubular member, means for joining together the distal extremities of the arms and electrical means extending through the flexible elongate tubular member and connected to the electrodes for performing electrical functions with respect to the electrodes, the at least one additional arm serving to urge the electrodes of the sector-shaped basket against the wall of the heart when the sector-shaped basket assembly is in the expanded position to permit high density mapping of the wall of the heart.

14. A probe as in claim 13 wherein the arms of the sector-shaped basket range between five and six in number.

15. A probe as in claim 13 wherein the arms of the sector-shaped basket lie within an angle of approximately 90° about the longitudinal axis.

16. A probe as in claim 13 wherein the arms of the sector-shaped basket lie with an angle of approximately 120° about the longitudinal axis.

17. A probe as in claim 13 wherein the sector-shaped basket has a longitudinal dimension which approximates the longitudinal dimension of the chamber of the heart.

18. A probe as in claim 13 wherein the electrodes include a pattern of closely-spaced electrodes for permitting high density mapping of a region of the wall.

19. A probe as in claim 18 wherein the sector-shaped basket has a longitudinal dimension significantly less than the longitudinal dimension of the chamber of the heart so as to permit the closely-spaced electrodes to be moved longitudinally within the chamber.

20. A probe as in claim 13 together with web-like means made of an elastomeric material disposed between the joined distal extremities of the arms the sector-shaped basket for inhibiting the formation of thrombus on the sector-shaped basket while the sector-shaped basket is disposed within the blood of the heart.

21. A probe as in claim 13 wherein the electrodes on adjacent arms are longitudinally offset relative to each other.

22. A mapping probe for introduction through a lumen into a chamber of a heart having blood therein and formed by a wall comprising a flexible elongate tubular member having proximal and distal extremities, a sector-shaped basket carried by the distal extremity of the flexible elongate tubular member and extending along a longitudinal axis, the sector-shaped basket having a plurality in excess of three longitudinally-extending spaced-apart arms with interconnected proximal extremities and interconnected distal extremities, the arms lying within an angle of approximately 180° or less about the longitudinal axis, a plurality of longitudinally spaced-apart electrodes carried by each of the arms and electrical means extending through the flexible elongate tubular member and connected to the electrodes for performing electrical functions with respect to the electrodes, the sector-shaped basket being movable between a contracted position for introduction through the lumen into the chamber and an expanded position for causing the electrodes to engage a portion of the wall of the heart to perform high density mapping of said portion of the wall of the heart.

23. A probe as in claim 22 wherein the arms lie within an angle of approximately 90° or less about the longitudinal axis.

24. A probe as in claim 23 wherein the arms range between five and six in number.

25. A probe as in claim 22 together with an elongate member having a proximal extremity carried by the distal extremity of the flexible elongate tubular member and a distal extremity, means for securing the distal extremity of the elongate member to the distal extremities of the arms, the elongate member serving to urge the sector-shaped basket against said portion of the wall of the heart.

26. A probe as in claim 25 wherein the elongate member consists of an additional arm which is disposed generally opposite the arms of the sector-shaped basket and is movable between a contracted position and an expanded position in which the additional arm bows outwardly from the longitudinal axis for engaging the wall of the heart generally opposite said portion.

27. A probe as in claim 22 wherein the arms each include a spring-like member which extends along the arm and has a predetermined shape for urging the sector-shaped basket to the expanded position.

28. A catheter for introduction through a lumen into a chamber of a heart having blood therein and formed by a wall comprising a flexible elongate tubular member having proximal and distal extremities and extending along a longitudinal axis, a sector-shaped basket carried by the distal extremity of the flexible elongate tubular member, the sector-shaped basket having a plurality of arms extending along the longitudinal axis, each of the arms having a plurality of longitudinally spaced-apart outwardly facing electrodes, all of the arms of the sector-shaped basket lying exclusively in a sector extending at right angles to the longitudinal axis within an angle of 180° or less whereby the electrodes carried by the arms can be urged against a portion of the wall of the heart by the sector-shaped basket for performing high density mapping of said portion of the wall.

29. A catheter as in claim 28 wherein each of the arms includes a shape memory alloy element.

30. A catheter as in claim 28 together with means for moving the sector-shaped basket from a collapsed position to an expanded position.

31. A catheter as in claim 28 together with means for yieldably urging the electrodes into engagement with the wall of the heart.

32. A catheter as in claim 31 wherein the means for yieldably urging includes an additional arm free of electrodes extending along the longitudinal axis generally opposite the sector-shaped basket.

33. A catheter as in claim 28 wherein the arms each have proximal and distal extremities, means interconnecting the proximal extremities of the arms and means interconnecting the distal extremities of the arms.

34. An apparatus for mapping a wall of a chamber of a heart comprising a flexible elongate member having proximal and distal extremities, expandable means carried by the distal extremity of the flexible elongate member, the expandable means movable between contracted and expanded positions and having a plurality of elongate flexible spaced-apart arms with distal extremities and means for joining together the distal extremities of the arms, a plurality of spaced-apart electrodes carried by the expandable means for engaging the wall of the heart when the expandable means is in its expanded position, the means for joining together the distal extremities of the arms including a distal tip formed from elastomeric material with a rounded distal end free of ridges for inhibiting the formation of trauma in the wall of the heart upon engagement of the tip with said wall.

35. An apparatus as in claim 34 wherein the an tip has a curved surface for providing a smooth transition between the tip and the arms to inhibit the formation of thrombus.

36. An apparatus as in claim 34 wherein the elastomeric material is silicone.

37. An apparatus as in claim 34 wherein the expandable means is a basket assembly having a plurality of spaced:a-part arms, a plurality of longitudinally spaced-apart electrodes carried by each of the arms for mapping the wall of the heart.

38. An apparatus as in claim 37 wherein the plurality of arms are circumferentially spaced apart.

39. An apparatus as in claim 37 wherein the plurality of arms are spaced relatively close together for permitting high density mapping of a portion of the wall of the heart.

40. A catheter for introduction into a body comprising a flexible elongate tubular member having proximal and distal extremities and extending along a longitudinal axis, first and second pluralities of arms extending along the longitudinal axis, each of the arms having a proximal extremity, means for attaching the proximal extremities of the arms to the distal extremity of the flexible elongate tubular member, said means including a first tubular member secured to the distal extremity of tile flexible elongate tubular member, the proximal extremities of the first plurality of arms circumferentially disposed about the first tubular member, a second tubular member concentrically mounted about the first tubular member for clamping the proximal extremities of the first plurality of arms between the first and second tubular members, the proximal extremities of the second plurality of arms circumferentially disposed about the second tubular member and a third tubular member concentrically mounted about the second tubular member for clamping the proximal extremities of the second plurality of arms between the second and third tubular members.

41. A catheter as in claim 40 wherein the proximal extremities of the first plurality of arms are circumferentially offset from the proximal extremities of the second plurality of arms.

42. A catheter as in claim 40 wherein the tubular members are each made from stainless steel.

43. A catheter as in claim 40 wherein each of the arms has a distal extremity, means for securing together the distal extremities of the arms.

44. A catheter as in claim 40 wherein the proximal extremities of the arms are circumferentially spaced-apart at equal intervals.

45. A catheter as in claim 40 wherein each of the arms has a plurality of longitudinally spaced-apart electrodes for engaging a wall of a heart.

\* \* \* \* \*